(12) United States Patent
Maisano et al.

(10) Patent No.: US 8,475,525 B2
(45) Date of Patent: Jul. 2, 2013

(54) TRICUSPID VALVE REPAIR USING TENSION

(75) Inventors: Francesco Maisano, Milan (IT); Hugo Vanermen, Knocke-le-Zoute (BE); Valery Perevalov, Kfar Saba (IL); Repheal Hof, Kfar Yona (IL)

(73) Assignee: 4Tech Inc., Waltham, MA (US)

( * ) Notice: Subject to any disclaimer, the term of this patent is extended or adjusted under 35 U.S.C. 154(b) by 269 days.

(21) Appl. No.: 12/692,061

(22) Filed: Jan. 22, 2010

(65) Prior Publication Data

US 2011/0184510 A1    Jul. 28, 2011

(51) Int. Cl.
*A61F 2/24*    (2006.01)
(52) U.S. Cl.
USPC ........... 623/2.37; 623/2.36; 623/1.36; 600/37
(58) Field of Classification Search
USPC ......................... 623/2.36, 2.37, 1.36; 600/37
See application file for complete search history.

(56) References Cited

U.S. PATENT DOCUMENTS

| | | |
|---|---|---|
| 4,493,329 A | 1/1985 | Crawford et al. |
| 4,625,727 A | 12/1986 | Leiboff |
| 4,778,468 A | 10/1988 | Hunt et al. |
| 5,108,420 A | 4/1992 | Marks |
| 5,330,521 A | 7/1994 | Cohen |
| 5,450,860 A | 9/1995 | O'Connor |
| 5,473,812 A | 12/1995 | Morris et al. |
| 5,776,178 A | 7/1998 | Pohndorf et al. |
| 5,843,120 A | 12/1998 | Israel et al. |
| 6,027,523 A | 2/2000 | Schmieding |
| 6,298,272 B1 | 10/2001 | Peterfeso et al. |
| 6,299,635 B1 | 10/2001 | Frantzen |
| 6,332,893 B1 | 12/2001 | Mortier et al. |
| 6,575,976 B2 | 6/2003 | Grafton |
| 6,613,078 B1 | 9/2003 | Barone |
| 6,613,079 B1 | 9/2003 | Wolinsky et al. |
| 6,616,684 B1 | 9/2003 | Vidlund et al. |
| 6,626,899 B2 | 9/2003 | Houser et al. |

(Continued)

FOREIGN PATENT DOCUMENTS

| | | |
|---|---|---|
| WO | 92/05093 A1 | 4/1992 |
| WO | 2005/021063 A2 | 3/2005 |

(Continued)

OTHER PUBLICATIONS

Shikhar Agarwal, et al; "Interventional Cardiology Perspective of Functional Tricuspid Regurgitation" Circulation: Cardiovascular Interventions, pp. 565-573; Dec. 2009; vol. 2, Issue 6.

(Continued)

*Primary Examiner* — Thomas J Sweet
*Assistant Examiner* — Seema Mathew
(74) *Attorney, Agent, or Firm* — Ladas & Parry LLP

(57) ABSTRACT

A method is provided, including implanting at least a first tissue-engaging element in a first portion of tissue in a vicinity of a heart valve of a patient, implanting at least a second tissue-engaging element in a portion of a blood vessel that is in contact with an atrium of a heart of the patient, and drawing at least a first leaflet of the valve toward at least a second leaflet of the valve by adjusting a distance between the portion of the blood vessel and the first portion of tissue in the vicinity of the heart valve of the patient. Other applications are also described.

20 Claims, 19 Drawing Sheets

U.S. PATENT DOCUMENTS

| | | | |
|---|---|---|---|
| 6,626,930 B1 | 9/2003 | Allen et al. | |
| 6,629,921 B1 | 10/2003 | Schweich, Jr. et al. | |
| 6,641,597 B2 | 11/2003 | Burkhart et al. | |
| 6,702,846 B2 | 3/2004 | Mikus et al. | |
| 6,723,038 B1 | 4/2004 | Schroeder et al. | |
| 6,730,118 B2 | 5/2004 | Spenser et al. | |
| 6,884,250 B2 | 4/2005 | Monassevitch et al. | |
| 7,101,395 B2 | 9/2006 | Tremulis et al. | |
| 7,125,421 B2 | 10/2006 | Tremulis et al. | |
| 7,144,363 B2 | 12/2006 | Pai et al. | |
| 7,159,593 B2 | 1/2007 | McCarthy et al. | |
| 7,169,187 B2 | 1/2007 | Datta et al. | |
| 7,175,625 B2 | 2/2007 | Culbert | |
| 7,186,262 B2 | 3/2007 | Saadat | |
| 7,201,772 B2 | 4/2007 | Schwammenthal et al. | |
| 7,311,728 B2 | 12/2007 | Solem et al. | |
| 7,316,706 B2 | 1/2008 | Bloom et al. | |
| 7,316,710 B1 | 1/2008 | Cheng et al. | |
| 7,338,506 B2 | 3/2008 | Caro | |
| 7,390,329 B2 | 6/2008 | Westra et al. | |
| 7,530,995 B2 | 5/2009 | Quijano et al. | |
| 7,547,321 B2 | 6/2009 | Silvestri et al. | |
| 7,549,983 B2 | 6/2009 | Roue et al. | |
| 7,618,449 B2 | 11/2009 | Tremulis et al. | |
| 7,628,797 B2 | 12/2009 | Tieu et al. | |
| 7,632,303 B1 | 12/2009 | Stalker et al. | |
| 7,771,467 B2 | 8/2010 | Svensson | |
| 7,780,726 B2 | 8/2010 | Seguin | |
| 7,803,187 B2 | 9/2010 | Hauser | |
| 7,988,725 B2* | 8/2011 | Gross et al. | 623/2.36 |
| 7,991,484 B1 | 8/2011 | Sengupta et al. | |
| 7,993,368 B2 | 8/2011 | Gambale et al. | |
| 8,010,207 B2 | 8/2011 | Smits et al. | |
| 8,108,054 B2 | 1/2012 | Helland | |
| 8,236,013 B2 | 8/2012 | Chu | |
| 8,262,725 B2* | 9/2012 | Subramanian | 623/2.36 |
| 8,267,981 B2 | 9/2012 | Boock et al. | |
| 8,332,051 B2 | 12/2012 | Sommer et al. | |
| 2002/0177904 A1 | 11/2002 | Huxel et al. | |
| 2003/0236568 A1 | 12/2003 | Hojeibane et al. | |
| 2004/0181287 A1 | 9/2004 | Gellman | |
| 2004/0186566 A1 | 9/2004 | Hindrichs et al. | |
| 2004/0193092 A1 | 9/2004 | Deal | |
| 2004/0236419 A1 | 11/2004 | Milo | |
| 2004/0260389 A1 | 12/2004 | Case et al. | |
| 2005/0016560 A1 | 1/2005 | Voughlohn | |
| 2005/0107812 A1 | 5/2005 | Starksen et al. | |
| 2005/0177228 A1 | 8/2005 | Solem et al. | |
| 2005/0203606 A1 | 9/2005 | VanCamp | |
| 2005/0216039 A1 | 9/2005 | Lederman | |
| 2006/0129166 A1 | 6/2006 | Lavelle | |
| 2006/0161265 A1 | 7/2006 | Levine et al. | |
| 2006/0229708 A1* | 10/2006 | Powell et al. | 623/1.24 |
| 2006/0241748 A1 | 10/2006 | Lee et al. | |
| 2006/0282161 A1 | 12/2006 | Huynh et al. | |
| 2007/0016287 A1 | 1/2007 | Cartledge et al. | |
| 2007/0049942 A1 | 3/2007 | Hindrichs et al. | |
| 2007/0049970 A1 | 3/2007 | Belef et al. | |
| 2007/0061010 A1* | 3/2007 | Hauser et al. | 623/2.36 |
| 2007/0066863 A1* | 3/2007 | Rafiee et al. | 600/37 |
| 2007/0093869 A1 | 4/2007 | Bloom et al. | |
| 2007/0118151 A1 | 5/2007 | Davidson | |
| 2007/0162107 A1 | 7/2007 | Haug et al. | |
| 2007/0198082 A1 | 8/2007 | Kapadia et al. | |
| 2007/0203391 A1 | 8/2007 | Bloom et al. | |
| 2007/0250160 A1 | 10/2007 | Rafiee | |
| 2007/0282375 A1 | 12/2007 | Hindrichs et al. | |
| 2008/0003539 A1 | 1/2008 | Lundgren | |
| 2008/0035160 A1 | 2/2008 | Woodson et al. | |
| 2008/0077231 A1 | 3/2008 | Heringes et al. | |
| 2008/0262609 A1 | 10/2008 | Gross et al. | |
| 2008/0288044 A1 | 11/2008 | Osborne | |
| 2008/0288062 A1* | 11/2008 | Andrieu et al. | 623/2.36 |
| 2009/0084386 A1 | 4/2009 | McClellan et al. | |
| 2009/0118776 A1 | 5/2009 | Kelsch et al. | |
| 2009/0149872 A1 | 6/2009 | Gross et al. | |
| 2009/0171439 A1 | 7/2009 | Nissl | |
| 2009/0216265 A1 | 8/2009 | DeVries et al. | |
| 2009/0259307 A1 | 10/2009 | Gross et al. | |
| 2009/0264995 A1* | 10/2009 | Subramanian | 623/2.36 |
| 2009/0326648 A1 | 12/2009 | Machold et al. | |
| 2010/0130992 A1 | 5/2010 | Machold et al. | |
| 2010/0161041 A1 | 6/2010 | Maisano et al. | |
| 2010/0161042 A1 | 6/2010 | Maisano et al. | |
| 2010/0161043 A1 | 6/2010 | Maisano et al. | |
| 2010/0161047 A1 | 6/2010 | Cabiri | |
| 2010/0168791 A1 | 7/2010 | Kassab et al. | |
| 2010/0174358 A1 | 7/2010 | Rabkin et al. | |
| 2010/0185278 A1* | 7/2010 | Schankereli | 623/2.36 |
| 2010/0211166 A1 | 8/2010 | Miller et al. | |
| 2010/0217382 A1 | 8/2010 | Chau et al. | |
| 2010/0234935 A1 | 9/2010 | Bashiri et al. | |
| 2010/0249908 A1 | 9/2010 | Chau et al. | |
| 2010/0280603 A1 | 11/2010 | Maisano et al. | |
| 2010/0280604 A1 | 11/2010 | Zipory et al. | |
| 2010/0280605 A1 | 11/2010 | Hammer et al. | |
| 2010/0286628 A1 | 11/2010 | Gross | |
| 2010/0286767 A1* | 11/2010 | Zipory et al. | 623/2.11 |
| 2010/0324598 A1 | 12/2010 | Anderson | |
| 2011/0022164 A1* | 1/2011 | Quinn et al. | 623/2.11 |
| 2011/0029066 A1 | 2/2011 | Gilad et al. | |
| 2011/0082538 A1* | 4/2011 | Dahlgren et al. | 623/2.11 |
| 2011/0087146 A1 | 4/2011 | Ryan et al. | |
| 2011/0093002 A1 | 4/2011 | Rucker et al. | |
| 2011/0106245 A1* | 5/2011 | Miller et al. | 623/2.11 |
| 2011/0106247 A1 | 5/2011 | Miller et al. | |
| 2011/0112632 A1 | 5/2011 | Chau et al. | |
| 2011/0184510 A1 | 7/2011 | Maisano et al. | |
| 2011/0238112 A1 | 9/2011 | Kim et al. | |
| 2012/0022640 A1* | 1/2012 | Gross et al. | 623/2.11 |
| 2012/0035712 A1 | 2/2012 | Maisano et al. | |
| 2012/0232373 A1 | 9/2012 | Hallander et al. | |
| 2013/0030522 A1* | 1/2013 | Rowe et al. | 623/2.36 |

FOREIGN PATENT DOCUMENTS

| | | |
|---|---|---|
| WO | 2005/102194 A2 | 11/2005 |
| WO | 2006/097931 A2 | 9/2006 |
| WO | 2008/068756 A2 | 6/2008 |
| WO | 2010/004546 A1 | 1/2010 |
| WO | 2010/073246 A2 | 7/2010 |
| WO | 2010/28502 A1 | 11/2010 |
| WO | 2010/128503 A2 | 11/2010 |
| WO | 2011/051942 A1 | 5/2011 |
| WO | 2011/089601 A1 | 7/2011 |
| WO | 2011/143263 A2 | 11/2011 |

OTHER PUBLICATIONS

Amplatzer Cardiac Plug Brochure (English Pages), AGA Medical Corporation Plymouth MN, Copyright 2008-2010, downloaded Jan. 11, 2011.

U.S. Appl. No. 60/902,146, filed Feb. 16, 2007.

An International Search Report and A Written Opinion, both dated May 19, 2011, which issued during the prosecution of Applicant's PCT/IL11/00064.

Francesco Maisano, et al; "The double-orifice technique as a standardized approach to treat mitral regurgitation due to severe myxomatous disease: surgical technique", European Journal of Cardio-thoracic Surgery, vol. 17, Issue 3, pp. 201-205; Mar. 2000.

Ottavio Alfieri, et al; "Novel Suture Device for Beating-Heart Mitral Leaflet Approximation", Ann Thorac Surg, vol. 74, Issue 5, Nov. 2002, pp. 1488-1493.

Smith & Nephew MINITAC™ TI 2.0 Suture Anchor Product Description, downloaded on Dec. 9, 2012 from http://global.smith-nephew.com/us/MINITAC_TI_2_SUTURE_ANCHR_3127.htm.

International Search Report and Written Opinion of the International Searching Authority; dated Jan. 22, 2013; International Appln. No. PCT/IL2012/000282.

* cited by examiner

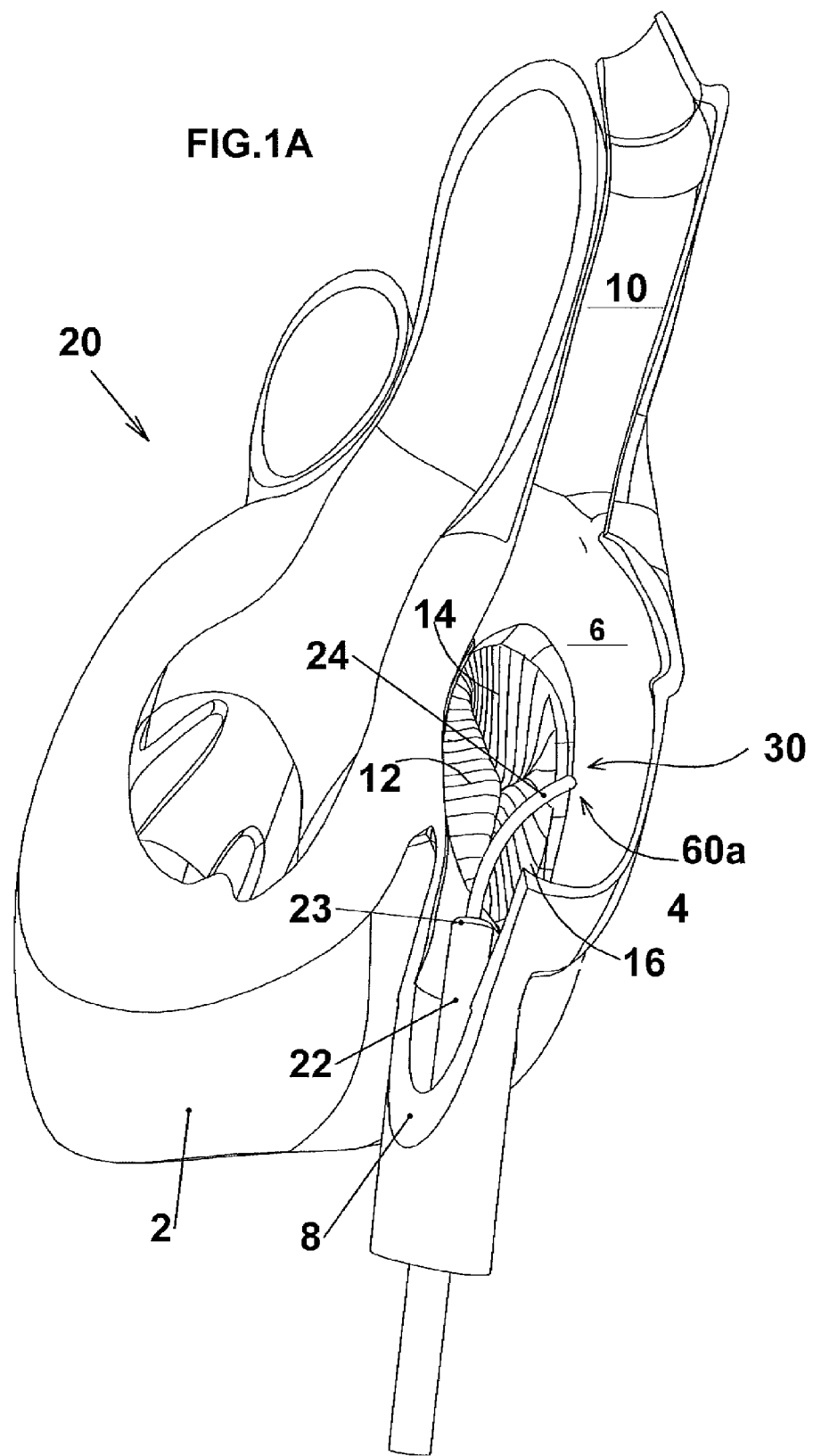

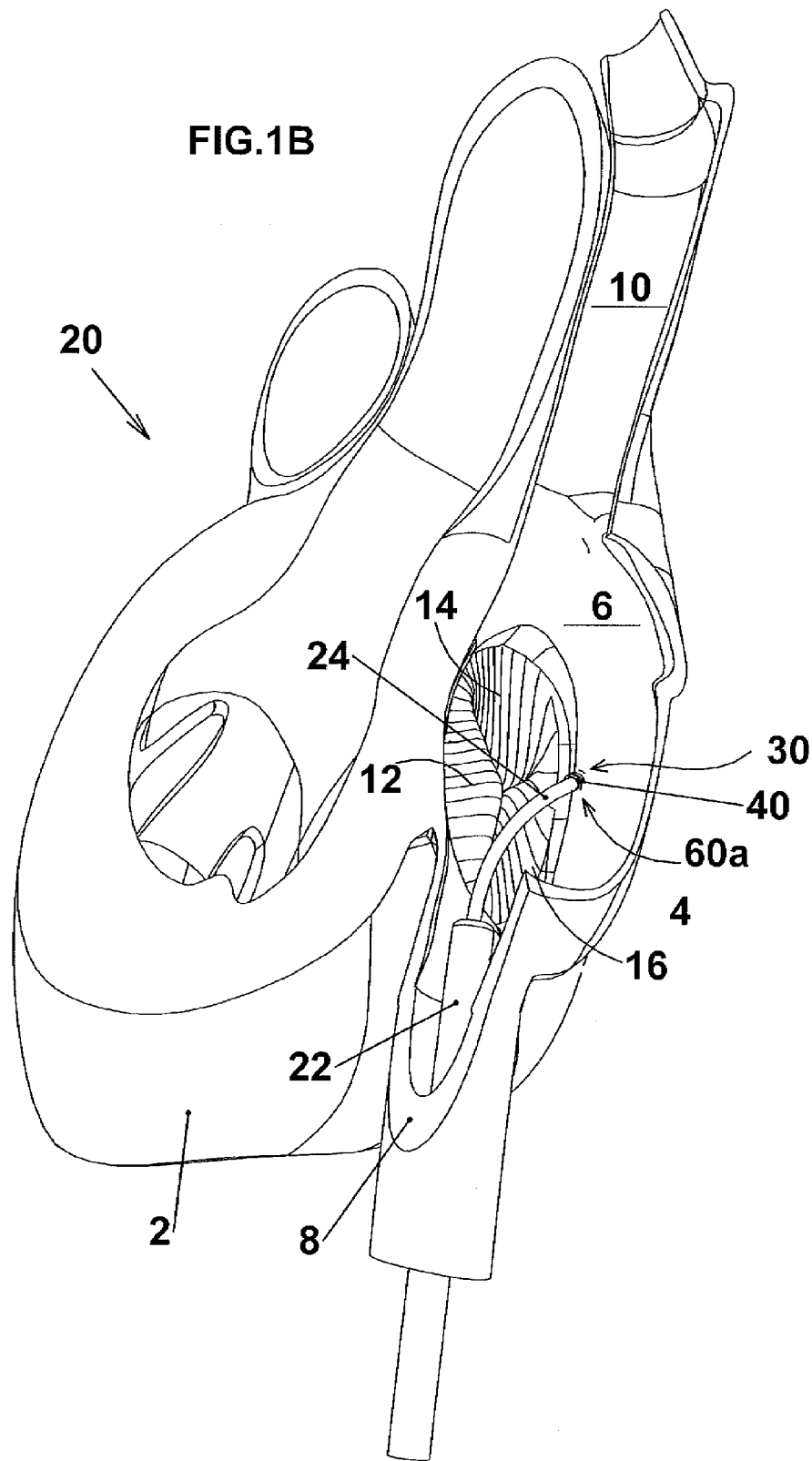

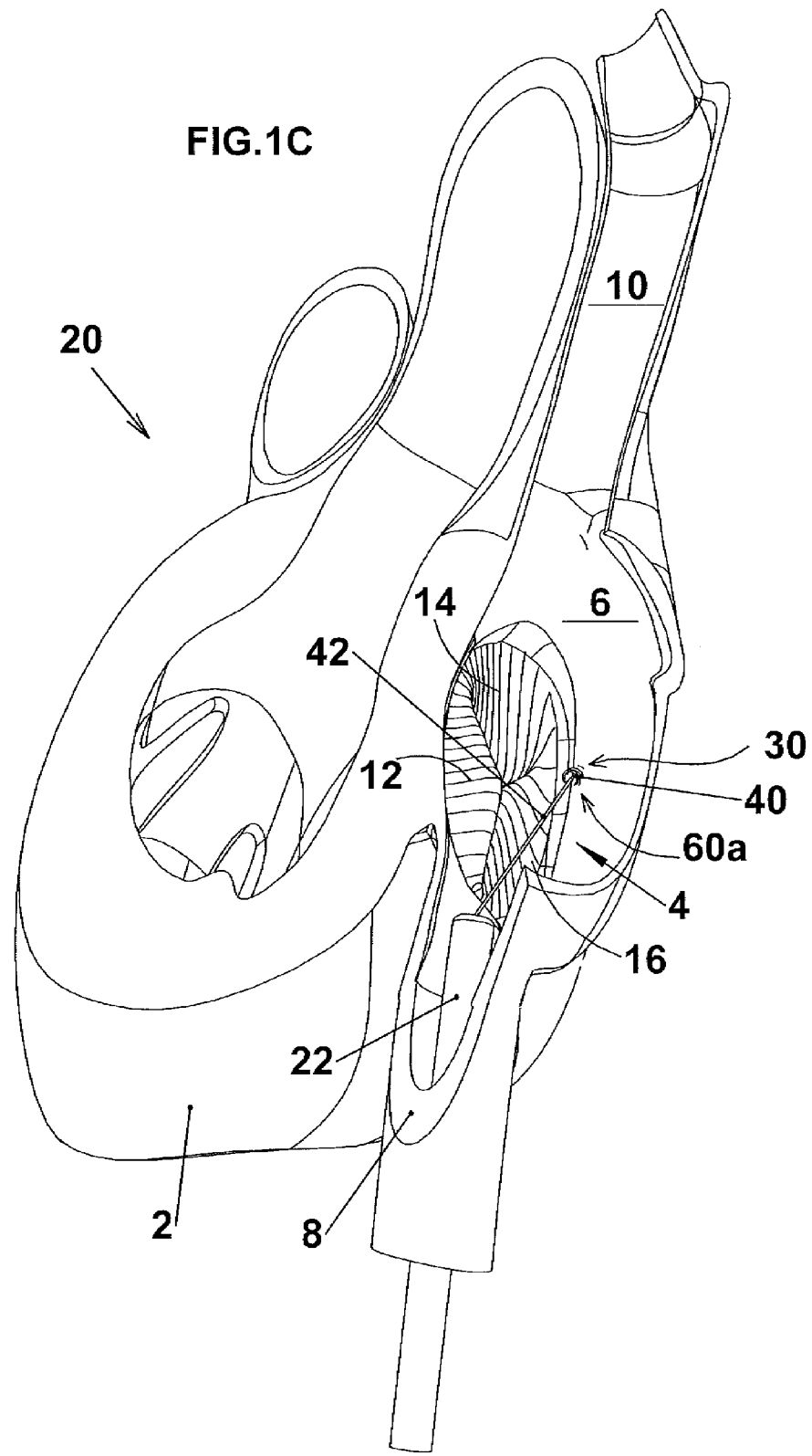

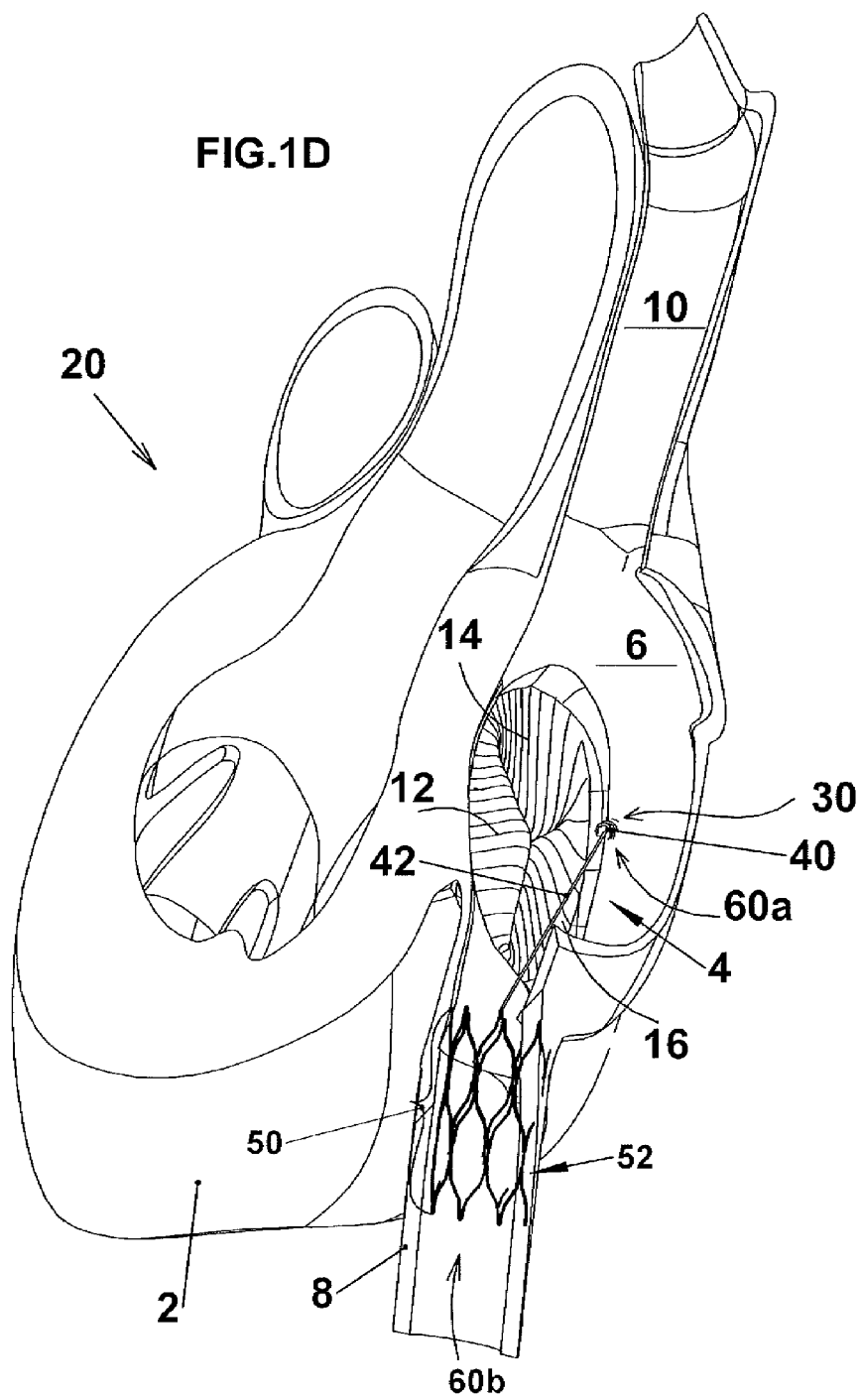

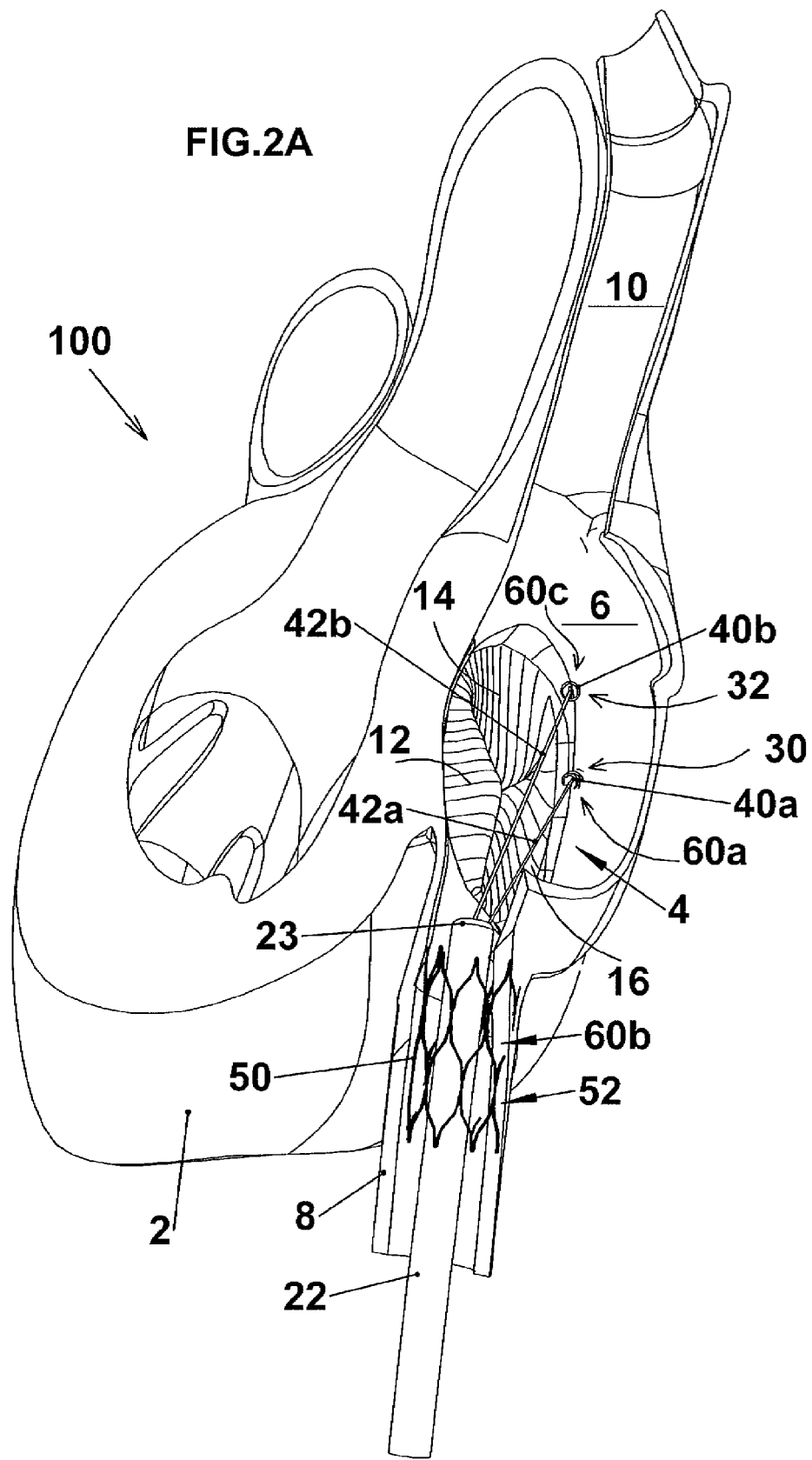

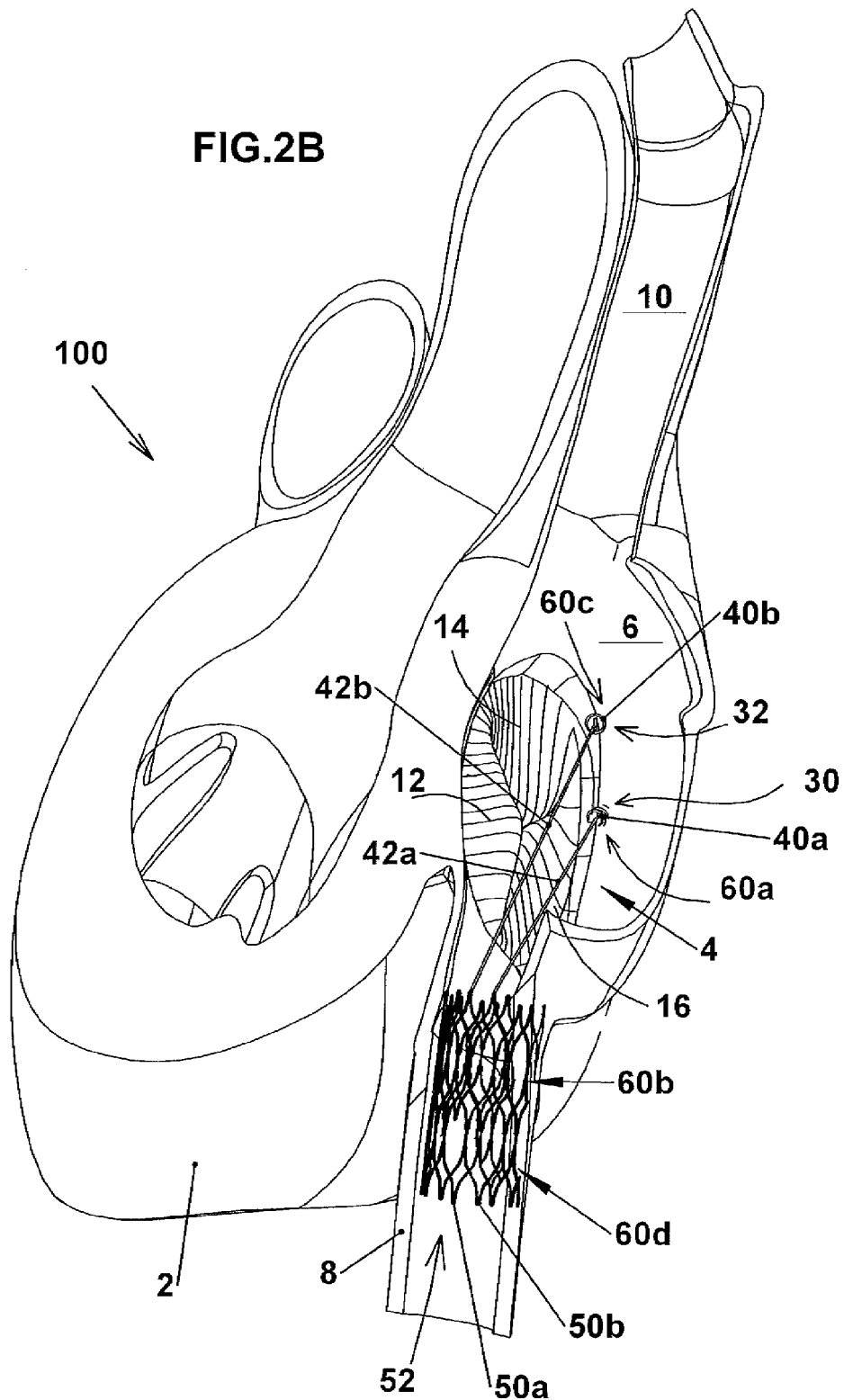

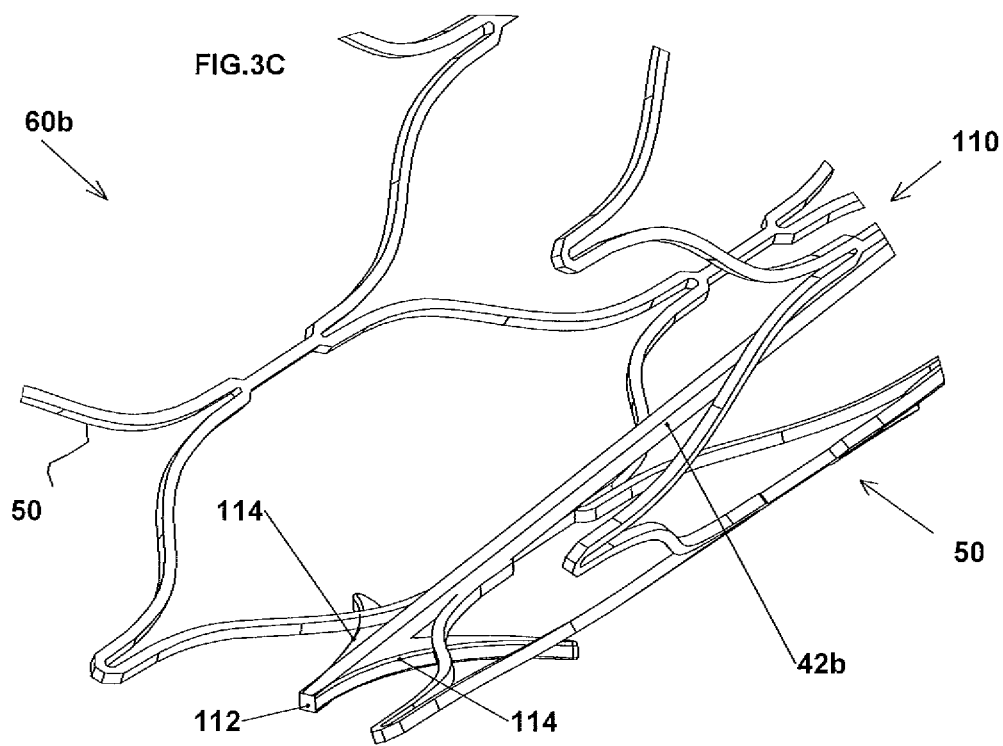

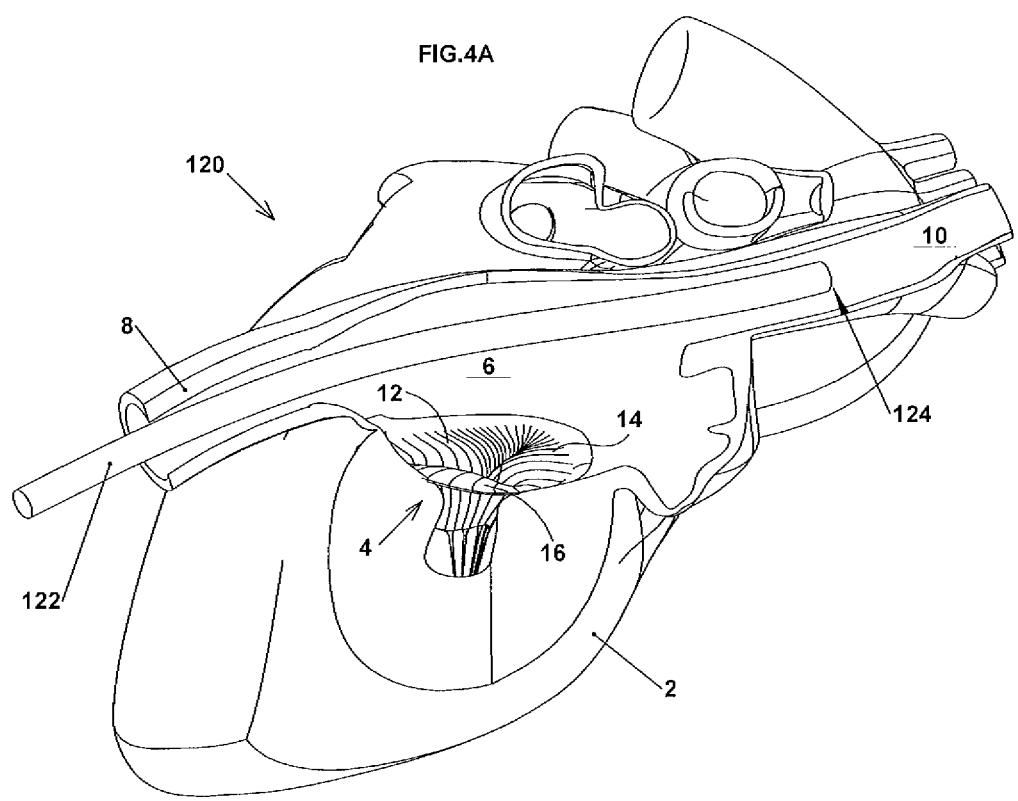

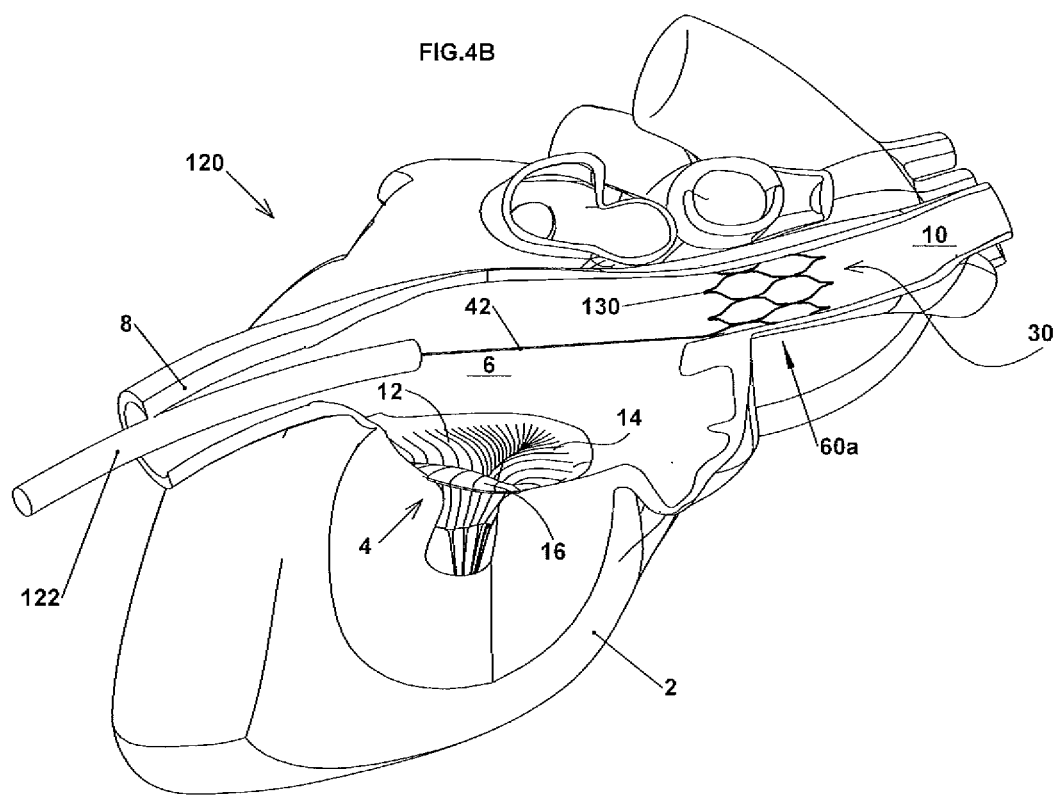

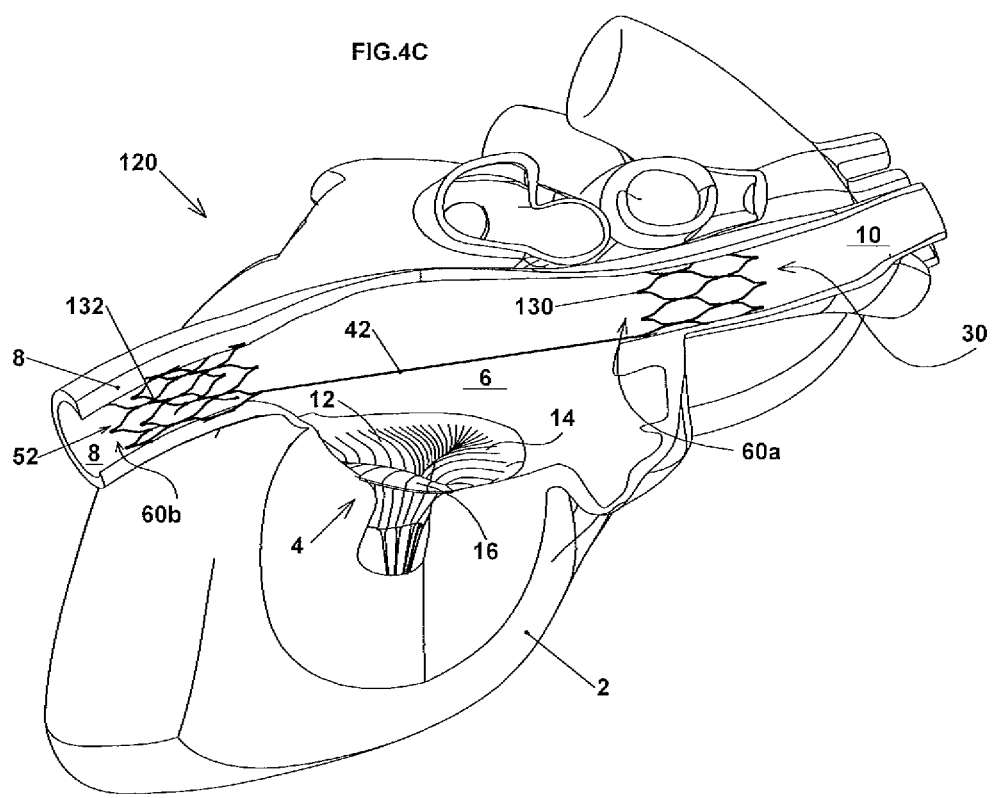

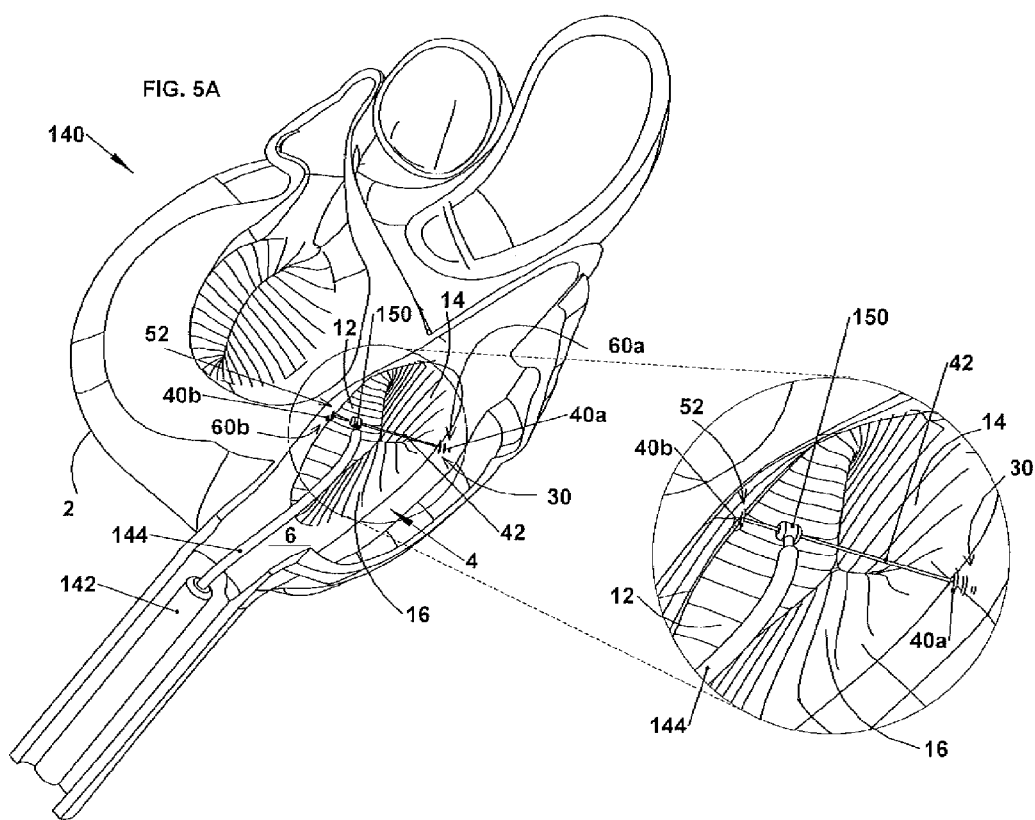

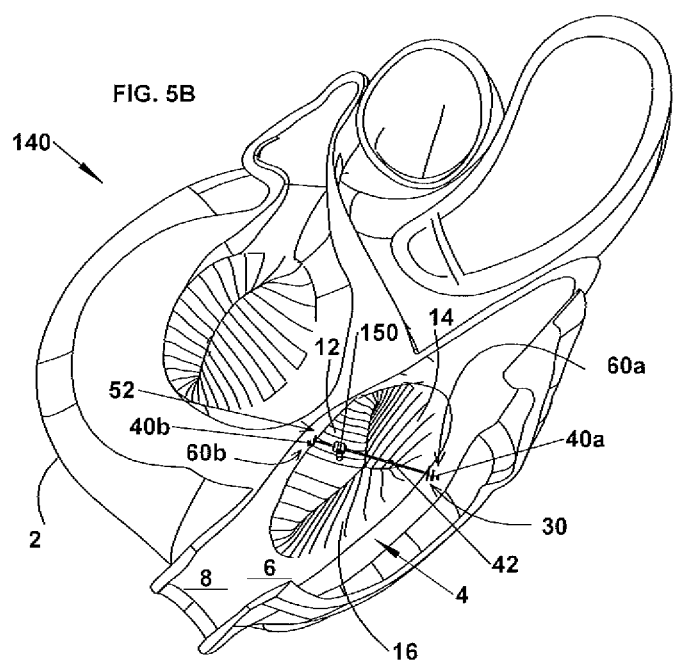

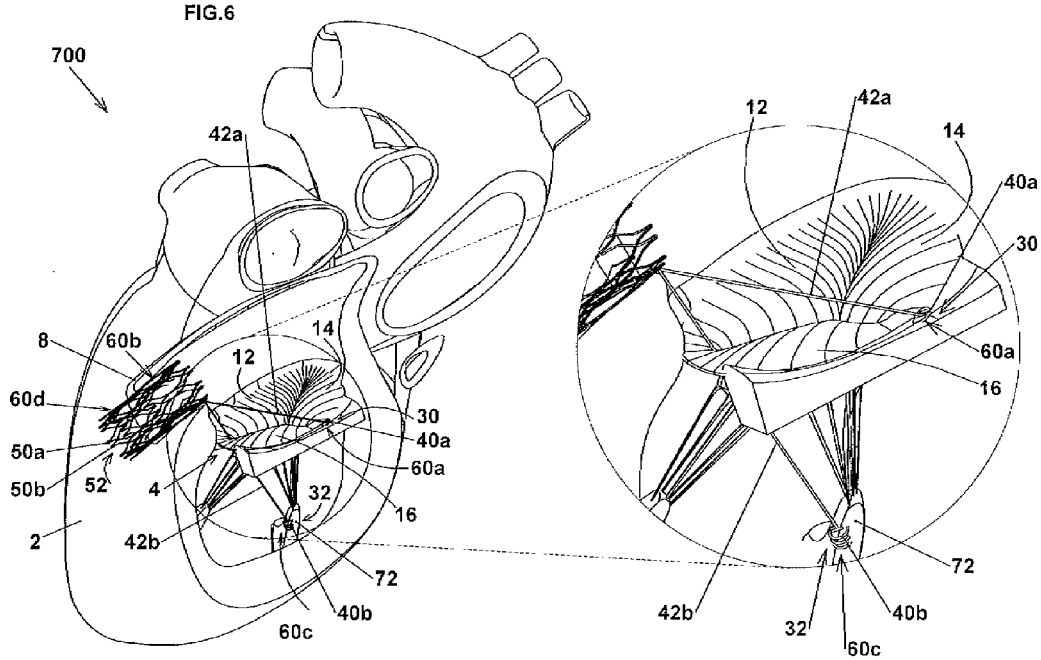

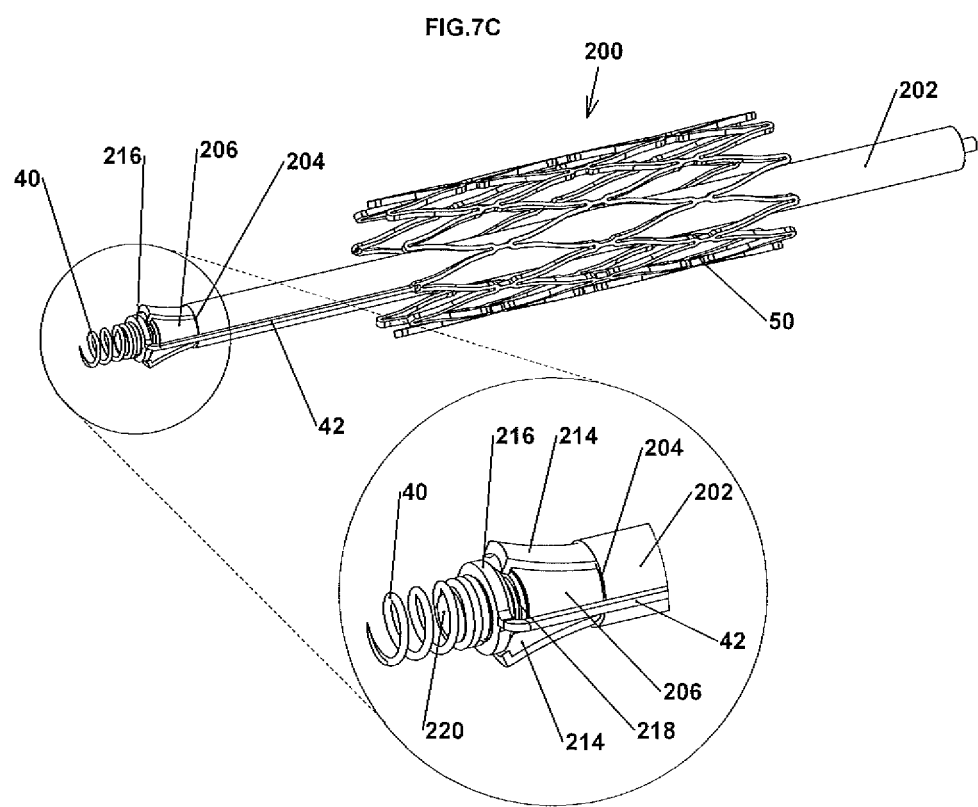

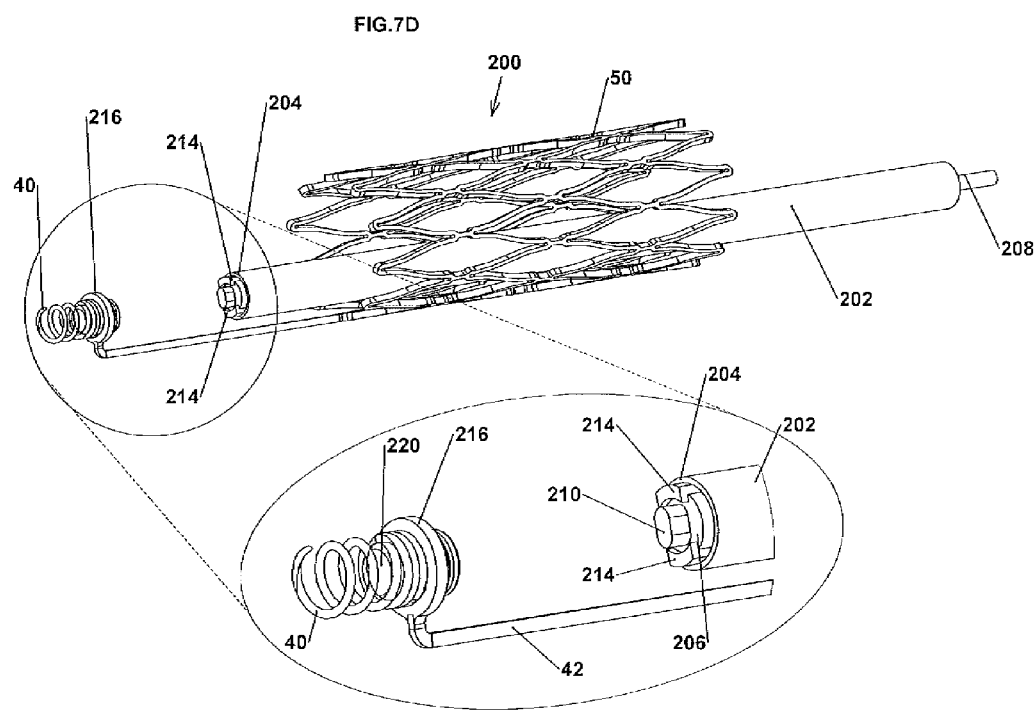

TRICUSPID VALVE REPAIR USING TENSION

FIELD OF THE INVENTION

Some applications of the present invention relate in general to valve repair. More specifically, some applications of the present invention relate to repair of a tricuspid valve of a patient.

BACKGROUND

Functional tricuspid regurgitation (FTR) is governed by several pathophysiologic abnormalities such as tricuspid valve annular dilatation, annular shape, pulmonary hypertension, left or right ventricle dysfunction, right ventricle geometry, and leaflet tethering. Treatment options for FTR are primarily surgical. The current prevalence of moderate-to-severe tricuspid regurgitation is estimated to be 1.6 million in the United States. Of these, only 8,000 patients undergo tricuspid valve surgeries annually, most of them in conjunction with left heart valve surgeries.

U.S. Pat. No. 7,530,995 to Quijano et al. describes a method of protecting an upper and a lower body of a patient from high venous pressures comprising: providing an elongate valve stent, wherein the stent comprises a first stent member with a first tissue valve secured to a first support structure being disposed at a first end of the stent and a second stent member with a second tissue valve secured to a second support structure being disposed at an opposite second end of the stent, wherein both support structures are collapsibly expandable, the second end being connected to the first end with at least one elongate connecting member; passing the elongate valve stent through a blood vessel with the first and second support structures in a collapsed position; and securing the first support structure to an inferior vena cava and the second support structure to a superior vena cava with both support structures in an expanded shape.

U.S. Pat. No. 7,159,593 to McCarthy et al. describes a method of protecting an upper body and a lower body of a patient from high venous pressures comprising implanting a first stented valve at the superior vena cava and a second stented valve at the inferior vena cava, wherein the first and second valves are configured to permit blood flow towards a right atrium of the patient and prevent blood flow in an opposite direction.

PCT Publication WO 05/021063 to Numamoto et al. describes an elongate valve stent and methods for protecting an upper or a lower body of a patient from high venous pressures comprising a stent member, the stent member comprising a support structure and a tissue valve, wherein the tissue valve is configured to permit fluid flow in one direction and prevent fluid flow in an opposite direction, and means for anchoring the stent member onto surrounding tissue of the superior vena cava or inferior vena cava.

U.S. Pat. No. 6,332,893 to Mortier et al. describes a device for heart valve repair including at least one tension member having a first end and second end. A basal anchor is disposed at the first end of the tension member and a secondary anchor at the second end. The method includes the steps of anchoring the basal anchor proximate a heart valve and anchoring the secondary anchor at a location spaced from the valve such that the chamber geometry is altered to reduce heart wall tension and/or stress on the valve leaflets.

The following patents and patent application publications may be of interest:
U.S. Pat. No. 5,450,860 to O'Connor
U.S. Pat. No. 6,626,899 to Houser et al.
U.S. Pat. No. 7,549,983 to Roue et al.
US Patent Application Publication 2005-0216039 to Lederman
US Patent Application Publication 2007-0118151 to Davidson
US Patent Application Publication 2007-0198082 to Kapadia et al.

SUMMARY OF EMBODIMENTS

In some applications of the present invention, apparatus and method are provided for repairing a tricuspid valve of a patient using tension. Typically, apparatus and method for repairing the tricuspid valve facilitate reducing of tricuspid valve regurgitation by altering the geometry of the tricuspid valve and/or by altering the geometry of the wall of the right atrium of the heart of the patient. In some applications of the present invention, a first tissue-engaging element is implanted in a first portion of tissue that is upstream of the tricuspid valve of the patient. A second tissue-engaging element is then implanted in a second portion of tissue that is upstream of the tricuspid valve of the patient. Typically, following implantation of both the first and second tissue-engaging elements, a distance between the leaflets of the tricuspid valve is adjusted by pulling a longitudinal member that connects the first and second tissue-engaging elements or by pulling at least one of the tissue-engaging elements. Alternatively or additionally, the longitudinal member is adjusted prior to implanting the second tissue-engaging element. For some applications, the longitudinal member is coupled at least in part to an adjusting mechanism, and the longitudinal member is pulled or relaxed responsively to actuation of the adjusting mechanism.

In some applications of the present invention, apparatus and method are provided to achieve bicuspidization of the tricuspid valve. For such applications, typically, the anterior leaflet and the septal leaflet are drawn together to enhance coaptation.

For some applications, the first tissue-engaging element comprises a first stent element which is expanded in a portion of an inferior vena cava. The second tissue engaging element comprises a second stent element which is expanded in a portion of a superior vena cava. The distance between the first and second stent elements is then adjusted by pulling the longitudinal member while monitoring regurgitation of the tricuspid valve. Responsively to the pulling of the longitudinal element, the geometry of the right atrium is altered, thereby drawing together the leaflets of the tricuspid valve.

For other applications, the first tissue-engaging element comprises a stent member that is implanted in either the inferior or superior vena cava, and the second tissue-engaging element comprises a tissue anchor which punctures a portion of cardiac tissue of the patient and is implanted at least in part in the portion of cardiac tissue.

For still other applications of the present invention, both the first and second tissue-engaging elements comprise respective first and second tissue anchors. Each tissue anchor punctures a respective portion of cardiac tissue of the patient and is implanted at least in part in the respective portion of cardiac tissue. The tensioning element couples the first and second tissue anchors and is adjusted following implantation of the first and second tissue anchors by pulling or relaxing the tensioning element.

There is therefore provided, in accordance with some applications of the present invention, a method, including:
implanting at least a first tissue-engaging element in a first portion of tissue in a vicinity of a heart valve of a patient;

implanting at least a second tissue-engaging element in a portion of a blood vessel that is in contact with an atrium of a heart of the patient; and drawing at least a first leaflet of the valve toward at least a second leaflet of the valve by adjusting a distance between the portion of the blood vessel and the first portion of tissue in the vicinity of the heart valve of the patient.

In some applications of the present invention, adjusting the distance between the portion of the blood vessel and the first portion of tissue in the vicinity of the heart valve of the patient includes pulling a longitudinal member that connects the first and second tissue-engaging elements.

In some applications of the present invention, adjusting the distance between the portion of the blood vessel and the first portion of tissue in the vicinity of the heart valve of the patient includes applying tension to one or more elements selected from the group consisting of the first tissue-engaging element and the second tissue-engaging element.

In some applications of the present invention, the method includes monitoring a level of regurgitation of the heart valve in conjunction with the adjusting the distance between the portion of the blood vessel and the first portion of tissue in the vicinity of the heart valve of the patient.

In some applications of the present invention, adjusting the distance between the portion of the blood vessel and the first portion of tissue in the vicinity of the heart valve of the patient includes pulling the first tissue-engaging element toward the portion of the blood vessel.

In some applications of the present invention, the heart valve includes a tricuspid valve, and adjusting the distance between the portion of the blood vessel and the first portion of tissue in the vicinity of the heart valve of the patient includes achieving bicuspidization of the tricuspid valve of the heart.

In some applications of the present invention, adjusting the distance between the portion of the blood vessel and the first portion of tissue in the vicinity of the heart valve of the patient includes actuating an adjusting mechanism that is coupled to a portion of a longitudinal member that connects the first and second tissue-engaging elements.

In some applications of the present invention, implanting the second tissue-engaging element in the portion of the blood vessel includes expanding a stent in the portion of the blood vessel.

In some applications of the present invention, the method includes:

implanting a third tissue-engaging element in a second portion of tissue of the heart, the third tissue-engaging element bring connected at a proximal end thereof to a distal end of a longitudinal member; and engaging a proximal end portion of the longitudinal member with the stent.

In some applications of the present invention, the method includes applying tension to the third tissue-engaging element.

In some applications of the present invention, implanting the first tissue-engaging element in the first portion of tissue in the vicinity of the heart valve of the patient includes engaging the first portion of tissue by performing one or more actions selected from the group consisting of: puncturing and squeezing the first portion of tissue and advancing at least a portion of the first tissue-engaging element into the first portion of tissue.

In some applications of the present invention:

the first portion of tissue in the vicinity of the heart valve includes a portion of tissue of that is opposite the portion of the blood vessel of the patient, engaging the first portion of tissue includes engaging the portion of tissue that is opposite the portion of the blood vessel of the patient, and drawing the first leaflet of the valve toward the second leaflet of the valve includes adjusting a distance between the portion of the blood vessel of the patient and the portion of tissue that is opposite the portion of the blood vessel of the patient.

In some applications of the present invention, the first portion of tissue in the vicinity of the heart valve includes a portion of tissue of an annulus of the valve, and engaging the first portion of tissue includes engaging the portion of tissue of the annulus of the valve.

In some applications of the present invention, the portion of tissue of the annulus of the valve includes a portion of tissue that is between a middle portion of an anterior leaflet of the valve and a middle portion of a posterior leaflet of the valve.

In some applications of the present invention, the first portion of tissue in the vicinity of the heart valve includes a portion of tissue of a wall of the atrium of the heart above an annulus of the valve, and engaging the first portion of tissue includes engaging the portion of tissue of the wall of the atrium.

There is additionally provided, in accordance with some applications of the present invention, a method, including:

implanting at least a first tissue-engaging element in a first portion of tissue upstream of a tricuspid valve of a patient;

implanting at least a second tissue-engaging element in a second portion of tissue upstream of the tricuspid valve of the patient; and altering a geometry of a wall of a right atrium of a heart of the patient by adjusting a distance between the first portion of tissue upstream of the tricuspid valve of the patient and the second portion of tissue upstream of the tricuspid valve of the patient.

In some applications of the present invention, adjusting the distance between the first portion of tissue upstream of the tricuspid valve of the patient and the second portion of tissue upstream of the tricuspid valve of the patient includes adjusting a distance between the first tissue-engaging element and the second tissue-engaging element.

In some applications of the present invention, the first portion of tissue includes a first portion of the wall of the right atrium, and implanting the first tissue-engaging element in the first portion of tissue upstream of the tricuspid valve of the patient includes implanting the first tissue-engaging element in the first portion of the wall of the right atrium.

In some applications of the present invention, the second portion of tissue includes a second portion of the wall of the right atrium, and implanting the second tissue-engaging element in the second portion of tissue upstream of the tricuspid valve of the patient includes implanting the second tissue-engaging element in the second portion of the wall of the right atrium.

In some applications of the present invention, the method includes monitoring a level of regurgitation of the tricuspid valve in conjunction with the altering the geometry of the wall of the right atrium.

In some applications of the present invention, adjusting the distance between the first portion of tissue upstream of the tricuspid valve of the patient and the second portion of tissue upstream of the tricuspid valve of the patient includes pulling a longitudinal element that connects the first and second tissue-engaging elements.

In some applications of the present invention, adjusting the distance between the first portion of tissue upstream of the tricuspid valve of the patient and the second portion of tissue upstream of the tricuspid valve of the patient includes actuating an adjusting mechanism that is coupled to a portion of a longitudinal element that connects the first and second tissue-engaging elements.

In some applications of the present invention, altering the geometry of the wall of the right atrium of the heart of the patient includes drawing together at least a first leaflet of the tricuspid valve of the patient and at least a second leaflet of the tricuspid valve of the patient.

There is further provided, in accordance with some applications of the present invention, a method, including:

engaging at least a portion of at least a first tissue-engaging element in a portion of tissue of a wall of an inferior vena cava of a patient;

engaging at least a portion of at least a second tissue-engaging element in a portion of tissue of a wall of a superior vena cava of the patient;

drawing at least a first leaflet of a heart valve toward at least a second leaflet of the valve by applying tension to one or more portions of tissue selected from the group consisting of: the portion of tissue of the wall of the inferior vena cava of the patient and the portion of tissue of the wall of the superior vena cava of the patient; and monitoring a level of regurgitation of a heart valve of the patient in conjunction with the applying of the tension.

In some applications of the present invention, applying the tension includes applying the tension following the engaging of the at least first tissue-engaging element and the engaging of the at least second tissue-engaging element.

In some applications of the present invention, applying the tension includes adjusting a distance between the portion of tissue of the wall of the inferior vena cava of the patient and the portion of tissue of the wall of the superior vena cava of the patient.

In some applications of the present invention, adjusting the distance between the portion of tissue of the wall of the inferior vena cava of the patient and the portion of tissue of the wall of the superior vena cava of the patient includes, by the applying of the tension, adjusting a distance between the first tissue-engaging element and the second tissue-engaging element.

In some applications of the present invention, engaging the portion of the at least first tissue-engaging element in the portion of tissue of the wall of the inferior vena cava of the patient includes expanding a first stent member in the inferior vena cava and contacting at least a portion of the first stent member with the portion of the wall of the inferior vena cava.

In some applications of the present invention, engaging the portion of the at least second tissue-engaging element in the portion of tissue of the wall of the superior vena cava of the patient includes expanding a second stent member in the inferior vena cava and contacting at least a portion of the first stent member with the portion of the wall of the inferior vena cava.

In some applications of the present invention, applying the tension includes altering a geometry of a wall of an atrium of a heart of the patient.

In some applications of the present invention, applying the tension includes pulling a longitudinal member that connects the at least first tissue-engaging element and the at least second tissue-engaging element.

In some applications of the present invention, applying the tension includes actuating an adjusting mechanism that is coupled to a portion of a tensioning element that connects the first and second tissue-engaging elements.

The present invention will be more fully understood from the following detailed description of applications thereof, taken together with the drawings, in which:

BRIEF DESCRIPTION OF THE DRAWINGS

FIGS. 1A-D are schematic illustrations of apparatus for reducing regurgitation of a heart valve which comprises a stent member, a tissue anchor, and a tensioning element that couples the stent member and the tissue anchor, in accordance with some applications of the present invention;

FIGS. 2A-B are schematic illustrations of apparatus for reducing regurgitation of the heart valve which comprises first and second stent members, first and second tissue anchor, and first and second tensioning elements, in accordance with some applications of the present invention;

FIGS. 3A-C are schematic illustrations of apparatus for reducing regurgitation of the heart valve which comprises a single stent member, first and second tissue anchor, and first and second tensioning elements, in accordance with some applications of the present invention;

FIGS. 4A-C are schematic illustrations of apparatus for reducing regurgitation of a tricuspid valve which comprises first and second stent members and first and a tensioning element that couples the first and second stent members, in accordance with some applications of the present invention;

FIGS. 5A-B are schematic illustrations of apparatus for reducing regurgitation of the heart valve which comprises first and second tissue anchors and a tensioning element that couples the first and second tissue anchors, in accordance with some applications of the present invention;

FIG. 6 is a schematic illustration of apparatus for reducing regurgitation of the heart valve which comprises a first anchoring system in the inferior vena cava, a first tissue anchor implanted at the valve, and a second tissue anchor implanted in the papillary muscle; and FIGS. 7A-D are schematic illustrations of a delivery system for a helical tissue anchor, in accordance with some applications of the present invention.

DETAILED DESCRIPTION OF THE EMBODIMENTS

Figure 3A:
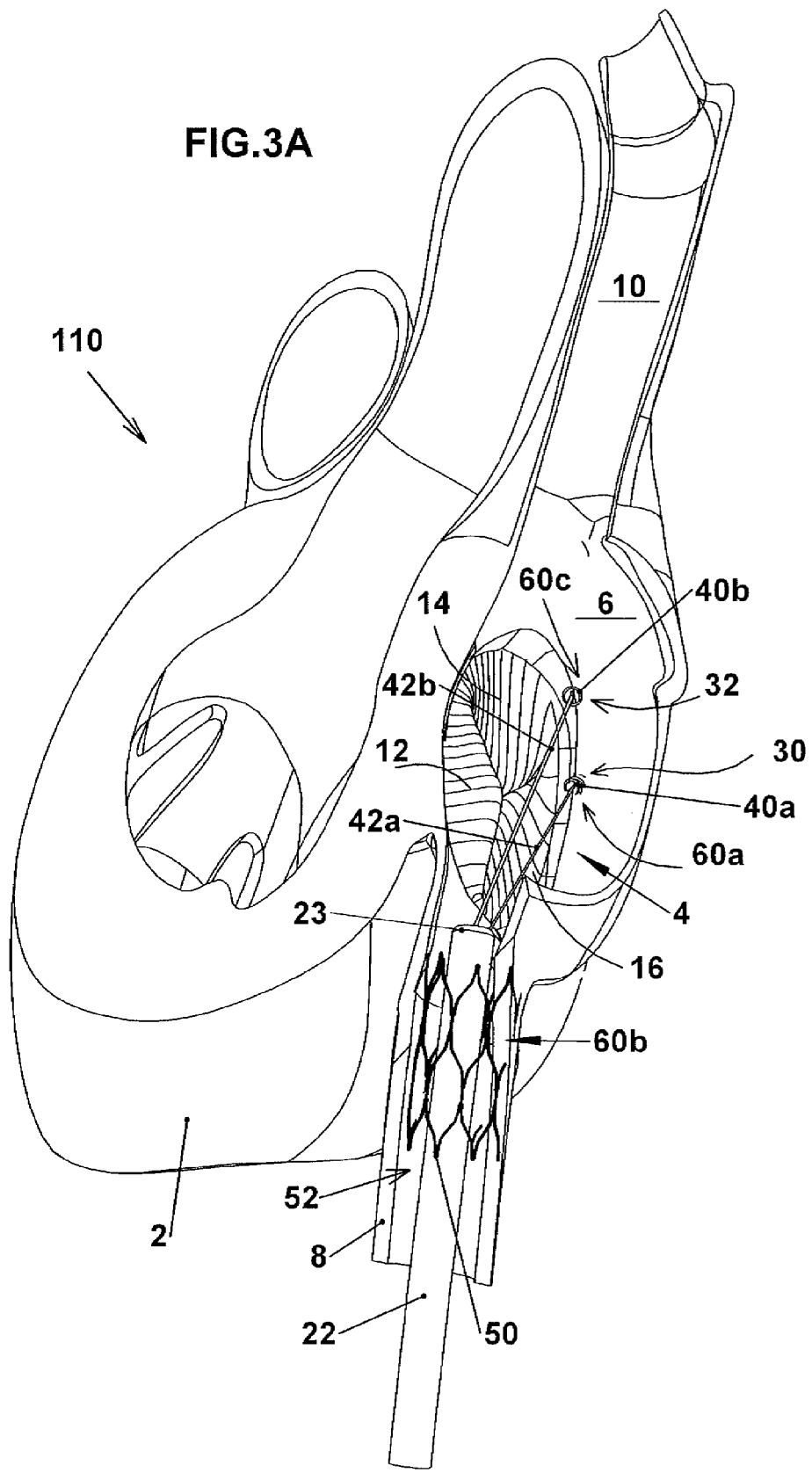

Reference is now made to FIGS. 1A-D, which are schematic illustrations of a system 20 comprising a first tissue-engaging element 60a and a second tissue-engaging element 60b for repairing a tricuspid valve 4 of a heart 2 of a patient, in accordance with some applications of the present invention. First tissue-engaging element 60a comprises a tissue anchor 40 which is designated for implantation at least in part in cardiac tissue at a first implantation site 30. It is to be noted that tissue anchor 40 comprises a helical tissue anchor by way of illustration and not limitation and that tissue anchor may comprise any tissue anchor for puncturing or clamping cardiac tissue. Second tissue-engaging element 60b comprises a stent member 50 which is designated for implantation in a portion of a blood vessel, e.g., a superior vena cava 10 or an inferior vena cava 8, at a second implantation site 52. First and second tissue-engaging elements 60a and 60b are coupled together by a flexible longitudinal member 42. Typically, a distance between first and second implantation sites 30 and 52 is adjusted by pulling to apply tension to or relaxing longitudinal member 42 and/or by applying tension to at least one of first and second tissue-engaging elements 60a and 60b. Responsively, a distance between the leaflets of tricuspid valve 4 is adjusted to reduce and eliminate regurgitation through valve 4, and thereby, valve 4 is repaired. For some applications, longitudinal member 42 is pulled or relaxed by manipulating second tissue-engaging element 60b, as is described hereinbelow.

Typically, first and second tissue-engaging elements 60a and 60b and longitudinal member 42 are fabricated from the same material, e.g., nitinol, from a single piece. That is, first and second tissue-engaging elements 60a and 60b and longitudinal member 42 define a single continuous implant unit. For some applications, at least second tissue-engaging element 60b and longitudinal member 42 are fabricated from a single piece.

For other applications, longitudinal member 42 comprises a flexible and/or superelastic material, e.g., nitinol, polyester, stainless steel, cobalt chrome, PTFE, or ePTFE. In some applications of the present invention, longitudinal member 42 comprises a braided polyester suture (e.g., Ticron). In other applications of the present invention, longitudinal member 42 is coated with polytetrafluoroethylene (PTFE). In some applications of the present invention, longitudinal member 42 comprises a plurality of wires that are intertwined to form a rope structure. For some applications, at least a part of longitudinal member 42 comprises a tension spring and/or a plurality of coils.

Second tissue-engaging element 60b comprises a stent member 50 which advanced toward and expandable in a portion of inferior vena cava 8, i.e., a blood vessel that is in direct contact with a right atrium 6 of heart 2 of the patient. Second tissue-engaging element 60b is implanted at second implantation site 52. As shown, first implantation site 30 comprises a portion of an annulus of tricuspid valve 4. Implantation site 30 typically comprises a portion of the annulus of valve 4 that is between (1) the middle of the junction between the annulus and anterior leaflet 14, and (2) the middle of the junction between the annulus and posterior leaflet 16, e.g., between the middle of the junction between the annulus and anterior leaflet 14 and the commissure between the anterior and posterior leaflets. That is, anchor 40 is screwed in the fibrous tissue of the tricuspid annulus close to the commissure in between anterior leaflet 14 and posterior leaflet 16. Implantation site 30 is typically close to the mural side valve 4. For such applications, the drawing together of first and second implantation sites 30 and 52 cinches valve 4 and creates a bicuspidization of tricuspid valve 4, and thereby achieve stronger coaptation between anterior leaflet 14 and septal leaflet 12.

For some applications, implantation site 30 may include a portion of tissue of a wall defining right atrium 6 of heart 2, typically in a vicinity of the annulus of valve 4. For other applications, first implantation site 30 may include a portion of a wall of a right ventricle of heart 2, a ventricular portion of the annulus of valve 4, or a portion of a papillary muscle of the right ventricle of heart 2, as is shown hereinbelow in FIG. 6. First implantation site 30 is typically a distance away from, e.g., generally opposite, second implantation site 52 so that, following adjusting of longitudinal member 42, first and second implantation sites 30 and 52 are drawn together, and thereby at least first and second leaflets, e.g., all three leaflets, of valve 4 are drawn toward each other. For applications in which first implantation site 30 includes a portion of tissue of the annulus, the adjusting of the distance between implantation sites 30 and 52 alters the geometry of (i.e., changes the configuration of) the annulus of valve 4 and thereby draws together the leaflets of valve 4. For applications in which first implantation site 30 includes tissue of a portion of a wall that defines atrium 6, the adjusting of the distance between implantation sites 30 and 52 alters the geometry of (i.e., changes the configuration of) the wall of atrium 6 and thereby draws together the leaflets of valve 4.

FIG. 1A shows the advancement of a catheter 22 toward atrium 6 of the patient until a distal end 23 of catheter is disposed within atrium 6, as shown. The procedure is typically performed with the aid of imaging, such as fluoroscopy, transesophageal echo, and/or echocardiography. For some applications, the procedure begins by advancing a semi-rigid guidewire into right atrium 6 of the patient. The guidewire provides a guide for the subsequent advancement of a catheter 22 therealong and into the right atrium. Once distal end 23 of catheter 22 has entered right atrium 6, the guidewire is retracted from the patient's body. Catheter 22 typically comprises a 14-20 F sheath, although the size may be selected as appropriate for a given patient. Catheter 22 is advanced through vasculature into right atrium 6 using a suitable point of origin typically determined for a given patient. For example:

catheter 22 may be introduced into the femoral vein of the patient, through inferior vena cava 8, and into right atrium 6;

catheter 22 may be introduced into the basilic vein, through the subclavian vein through superior vena cava 10, and into right atrium 6; or catheter 22 may be introduced into the external jugular vein, through the subclavian vein through superior vena cava 10, and into right atrium 6.

As shown in FIG. 1A, catheter 22 is advanced through inferior vena cava 8 of the patient and into right atrium 6 using a suitable point of origin typically determined for a given patient.

Once distal end 23 of catheter 22 is disposed within atrium 6, an anchor-deployment tube 24 extends from within catheter 22 beyond distal end 23 thereof and toward first implantation site 30. Anchor-deployment tube 24 holds tissue anchor 40 and a distal portion of longitudinal member 42. For some applications, tube 24 is steerable, as is known in the catheter art, while for other applications, a separate steerable element may be coupled to anchor-deployment tube 24. Under the aid of imaging guidance, anchor-deployment tube 24 is advanced toward first implantation site 30 until a distal end 26 thereof contacts cardiac tissue of heart 2 at first implantation site 30. Anchor-deployment tube 24 facilitates atraumatic advancement of first tissue-engaging element 60a toward first implantation site 30. For such an application in which anchor-deployment tube 24 is used, stent 50 is compressed within a portion of tube 24.

An anchor-manipulating tool (not shown for clarity of illustration), that is slidably disposed within anchor-deployment tube 24, is slid distally within tube so as to push distally tissue anchor 40 of first tissue-engaging element 60a and expose tissue anchor 40 from within tube 24. For some applications of the present invention, the anchor-manipulating tool is reversibly coupled to anchor 40 and facilitates implantation of anchor 40 in the cardiac tissue. For applications in which anchor 40 comprises a helical tissue anchor, as shown, the operating physician rotates the anchor-manipulating tool from a site outside the body of the patient in order to rotate anchor 40 and thereby corkscrew at least a portion of anchor 40 in the cardiac tissue.

Alternatively, system 20 is provided independently of the anchor-manipulating tool, and anchor-deployment tube 24 facilitates implantation of anchor 40 in the cardiac tissue. For applications in which anchor 40 comprises a helical tissue anchor, as shown, the operating physician rotates anchor-deployment tube 24 from a site outside the body of the patient in order to rotate anchor 40 and thereby corkscrew at least a portion of anchor 40 in the cardiac tissue.

It is to be noted that for some applications of the present invention, anchor 40 comprises a clip, jaws, or a clamp which grips and squeezes a portion of cardiac tissue and does not puncture the cardiac tissue.

Following the implantation of anchor 40 at first implantation site 30, anchor-deployment tube 24 is retracted within catheter 22 in order to expose longitudinal member 42, as shown in FIG. 10. Subsequently, longitudinal member 42 is pulled taut in order to repair tricuspid valve 4, as described hereinbelow.

For some applications, prior to pulling the portion of longitudinal member 42 that is disposed between anchor 40 and distal end 23 of catheter 22, a mechanism that facilitates the application of a pulling force to longitudinal member 42 is fixed in place, as will be described hereinbelow. This fixing in place provides a reference force to system 20 while applying tension to longitudinal member 42 so as to ensure that during the pulling of longitudinal member 42, stent 50 is not pulled from within catheter 22. For some applications, distal end 23 of catheter 22 is fixed in place with respect to longitudinal member 42. Fixing in place catheter 22 stabilizes catheter 22 as longitudinal member 42 is pulled. This enables distal end 23 to remain in place and not slide distally toward implantation site 30 during the adjusting of longitudinal member 42. For some applications of the present invention, a proximal portion of catheter 22 and/or a proximal handle portion coupled to catheter 22 is anchored or otherwise fixed in place at its access location, e.g., by taping or plastering. Alternatively or additionally, a distal portion of catheter 22 comprises an inflatable element coupled to an inflation conduit which runs the length of catheter 22 from the distal portion thereof to a site outside the body of the patient. Prior to the adjusting of longitudinal member 42, the inflatable element is inflated such that it contacts tissue of the vasculature through which catheter 22 is advanced, and thereby catheter 22 is fixed in place. Typically, the inflatable element comprises an annular inflatable element, such that when inflated, the annular inflatable element functions as a seal to hold in place the distal portion of catheter 22.

Following the fixation of the mechanism that facilitates pulling of longitudinal member 42, the physician then pulls longitudinal member 42 and thereby draws together first and second implantation sites 30 and 52.

For some applications, catheter 22 is reversibly coupled to a proximal portion of longitudinal member 42 by being directly coupled to the proximal portion of member 42 and/or catheter 22 is reversibly coupled to second tissue-engaging element 60*b*. For example, catheter 22 may be reversibly coupled to stent 50 by the stent's application of a radial force against the inner wall of catheter 22 because of the tendency of stent 50 to expand radially. Following implantation of first tissue-engaging element 60*a*, catheter 22 (or an element disposed therein) is then pulled proximally to apply tension to longitudinal member 42, which, in such an application, functions as a tensioning element. For some applications, catheter 22 pulls on second tissue-engaging element 60*b* in order to pull longitudinal member 42. For other applications, catheter 22 pulls directly on longitudinal member 42. For yet other applications, a pulling mechanism pulls on longitudinal member 42, as is described hereinbelow with reference to FIGS. 7A-D.

Pulling longitudinal member 42 pulls taut the portion of longitudinal member 42 that is disposed between anchor 40 and distal end 23 of catheter 22. Additionally, longitudinal member 42 may be pulled or relaxed in order to adjust the distance between first and second implantation sites 30 and 52. Responsively to the pulling of longitudinal member 42, at least the anterior and septal leaflets of tricuspid valve 4 are drawn together because the geometry of the annulus and/or of the wall of atrium 6 is altered in accordance with the pulling of longitudinal member 42 and depending on the positioning of first tissue-engaging element 60*a*. During the pulling of longitudinal member 42 by catheter 22, a level of regurgitation of tricuspid valve 4 is monitored. Longitudinal member 42 is pulled until the regurgitation ceases.

Once the physician determines that the regurgitation of valve 4 ceases, and valve 4 has been repaired, the physician decouples catheter 22 from second tissue-engaging element 60*b* disposed therein and/or from longitudinal member 42, and then retracts catheter 22 in order to expose second tissue-engaging element 60*b*, i.e., stent member 50, as shown. During the advancement of catheter 22 toward atrium 6, stent member 50 is disposed within a distal portion of catheter 22 in a compressed state. Following initial retracting of catheter 22, stent member 50 is exposed and is allowed to expand and contact a wall of inferior vena cava 8, as shown in FIG. 1D. Responsively to the expanding, stent member 50 is implanted in second implantation site 52 and maintains the tension of longitudinal member 42 on anchor 40 and thereby on the portion of cardiac tissue to which anchor 40 is coupled.

Reference is now made to FIGS. 1A-D. It is to be noted that catheter 22 may enter via superior vena cava 10, as described hereinabove. For such applications, first implantation site 30 may comprise an area of the annulus of valve 4, or a portion of the wall defining atrium 6 that is opposite superior vena cava 10.

Reference is again made to FIGS. 1A-D For some applications, following the implantation of first and second tissue-engaging elements 60*a* and 60*b*, a distance between first and second tissue-engaging elements 60*a* and 60*b* is adjusted by an adjustable mechanism, as described hereinbelow with reference to FIGS. 5A-B. In such applications, a length of longitudinal member 42 between first and second tissue-engaging elements 60*a* and 60*b* may be adjusted by an adjusting mechanism 150, as shown in FIGS. 5A-B. Adjusting mechanism 150 typically comprises a mechanical element which shortens a distance of longitudinal member 42 between first and second tissue-engaging elements 60*a* and 60*b*. For some applications, adjustable mechanism 150 may be permanently coupled to longitudinal member 42 (not shown) and comprises an adjusting element, e.g., a spool for looping portions of longitudinal member 42 therearound, a crimping bead for crimping and shortening a portion of longitudinal member 42, a ratchet element, or a deforming element which deforms a portion of longitudinal member 42 in order to shorten its length between first and second tissue-engaging elements 60*a* and 60*b*. For other applications, adjusting mechanism 150 comprises only an adjusting tool 144, as shown in FIG. 5A. In such applications, adjusting tool 144 may comprise an adjusting element, e.g., a crimping bead for crimping and shortening a portion of longitudinal member 42, or a deforming element which deforms a portion of longitudinal member 42 in order to shorten its length between first and second tissue-engaging elements 60*a* and 60*b*. In either application, a level of regurgitation of valve 4 is monitored during the adjusting of the distance between first and second tissue-engaging elements 60*a* and 60*b* by adjusting mechanism 150.

Reference is now made to FIGS. 7A-D, which are schematic illustrations of a delivery tool system 200 for implanting anchor 40, in accordance with some applications of the present invention.

Figure 7A:
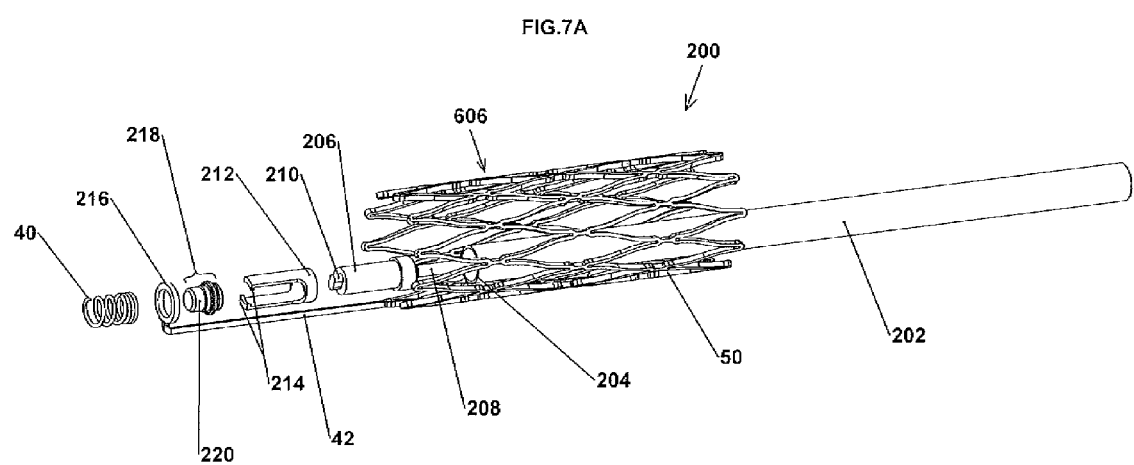

Reference is now made to FIGS. 1A-D and 7A-D. It is to be noted that anchor 40 may be implanted using delivery tool system 200. FIG. 7A shows an exploded view of the components of delivery tool system 200 and its spatial orientation relative to stent 50, longitudinal member 42, and anchor 40. In such an application, a distal end of longitudinal member 42 comprises an annular loop 216 through which a portion of anchor 40 is coupled to the distal end of longitudinal member 42. In such an application, stent 50, longitudinal member 42, and anchor 40 are not fabricated from the same piece, as described hereinabove; rather, only stent 50, longitudinal member 42, and annular loop 216 are fabricated from a single piece, and anchor 40 is coupled to longitudinal member 42 via annular loop 216.

Figure 7B:
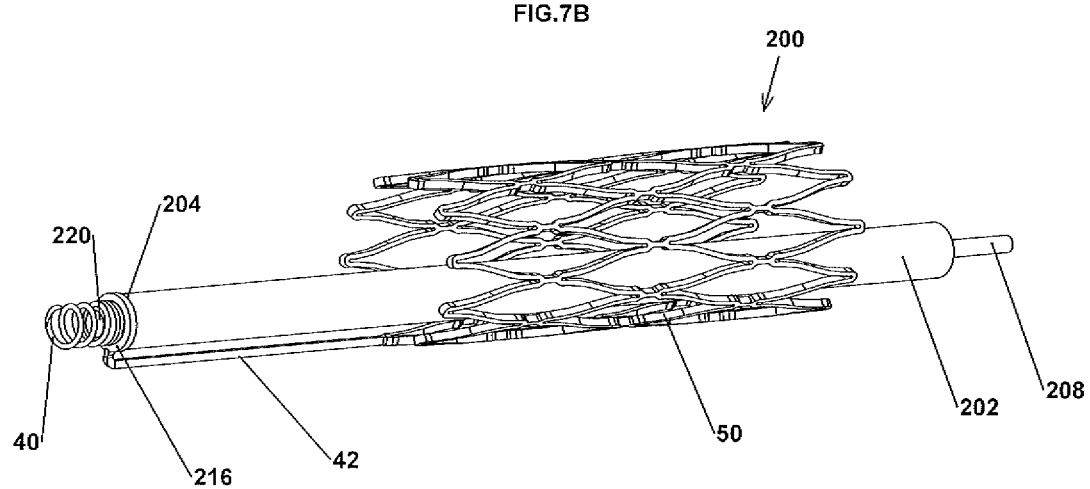

System 200 comprises an adapter 218, which is shaped so as to define an annular proximal portion and a distal cylindrical portion having a distal end 220. During the manufacture of system 200, distal end 220 of the cylindrical portion of adapter 218 is slid through annular loop 218 at the distal end of longitudinal member 42, thereby coupling adapter 218 to the distal end of longitudinal member 42. Distal end 220 of adapter 218 is then welded or otherwise fixedly coupled to a proximal portion of an inner lumen of anchor 40, as shown in FIG. 7B. This coupling arrangement of anchor 40 to annular loop 216 and adapter 218 enables anchor 40 to rotate about a central longitudinal axis of delivery system 200, freely within annular loop 216. That is, delivery tool system 200 rotates anchor 40 without rotating longitudinal member 42 and stent 50, as described herein below.

Delivery tool system 200 comprises a delivery tool overtube 202 having a distal end thereof. Delivery tool overtube 202 is housed within catheter 22 such that a distal portion thereof passes in part through the lumen of stent 50 and a distal end 204 thereof extends toward tissue anchor 40. During delivery of tissue anchor 40 and stent 50 toward their respective implantation sites, deliver tool system 200 assumes the configuration shown in FIG. 7B. It is to be noted, however, that stent 50 is compressed around the portion of overtube 202 that extends through the lumen of stent 50 (not shown for clarity of illustration), and that catheter 22 (not shown for clarity of illustration) surrounds system 200 (and thereby compresses stent 50).

Reference is again made to FIG. 7A. Overtube 202 houses a torque-delivering and an anchor-pulling tube 208 and facilitates slidable coupling of tube 208 to overtube 202. A distal end of torque-delivering and an anchor-pulling tube 208 is coupled to a manipulator 206 which is shaped so as to define a coupling 210 which couples manipulator to adapter 218, and thereby, to anchor 40. In order to rotate anchor 40, torque-delivering and an anchor-pulling tube 208 is rotated. As torque-delivering and an anchor-pulling tube 208 is rotated, manipulator 206 is rotated in order to corkscrew anchor 40 into the cardiac tissue of the patient. As adapter 218 rotates, the cylindrical portion thereof rotates freely within annular loop 216. This coupling arrangement of adapter 218 (and thereby anchor 40) to loop 216 (and thereby longitudinal member 42) enables the physician to rotate and implant anchor 40 without rotating longitudinal member 42 and stent 50.

Following rotation of anchor 40, torque-delivering and an anchor-pulling tube 208 is pulled by the physician in order to pull on anchor 40 and thereby on the portion of cardiac tissue to which anchor 40 is implanted at first implantation site 30. Tube 208 is typically coupled at a proximal end thereof to a mechanical element, e.g., a knob, at the handle portion outside the body of the patient. The physician pulls on tube 208 by actuating the mechanical element that is coupled to the proximal end of tube 208. This pulling of tube 208, and thereby of anchor 40 and of cardiac tissue at first implantation site 30, draws first implantation site toward second implantation site 52 and thereby draws at least anterior leaflet 14 toward septal leaflet 12 in order to achieve coaptation of the leaflets and reduce regurgitation through valve 4.

Following the pulling of anchor 40, stent 50 is positioned at second implantation site 52. Catheter 22 is then retracted slightly along tube 202 so as to pull taut longitudinal member 42 and to ensure that tension is maintained at first implantation site 30 and along longitudinal member 42. Stent 50 is then deployed when the physician holds torque-delivering and anchor-pulling tool 208 and then retracts proximally either (1) catheter 22 or (2) a sheath (i.e., that disposed within catheter 22 and surrounds stent 50), around stent 50 so as to deploy stent 50 from within either (1) catheter 22 or (2) the sheath disposed within catheter 22.

It is to be noted that stent 50 is retrievable following at least partial deployment thereof, e.g., following deployment of up to ½ or up to ⅓ of stent 50. In such an application, following the initial retraction proximally of catheter 22 from around stent 50 in order to deploy at least a distal portion of stent 50, catheter 22 is advanceable distally so as to compress and retrieve the at least partially-deployed stent back into the distal end portion of catheter 22. Alternatively, catheter 22 houses a sheath which compresses stent 50 during delivery of stent to second implantation site 52. During the initial retracting of catheter 22 proximally, the sheath surrounding stent 50 is also retracted in conjunction with the retracting of catheter 22. Following the at least partial deployment of stent 50 in order to deploy at least a distal portion of stent 50, the sheath is advanceable distally (while catheter 22 remains in place) so as to compress and retrieve the at least partially-deployed stent back into the distal end portion of the sheath. The sheath is then retracted into catheter 22. For such applications of the present invention in which stent 50 is retrievable following at least partial deployment thereof, anchor 40 can then be unscrewed from first implantation site 30 and the entire implant system may be extracted from the body, or repositioned in the heart, depending on the need of a given patient.

For applications in which stent 50 is retrievable, in order to retrieve stent 50 (i.e., prior to the decoupling of manipulator 206 from adapter 218 and thereby from anchor 40), the physician holds torque-delivering and anchor-pulling tool 208 and then advances distally either (1) catheter 22 or (2) the sheath disposed within catheter 22, around stent 50 so as to compress stent 50 within either (1) catheter 22 or (2) the sheath disposed within catheter 22. Torque-delivering and anchor-pulling tool 208 may then be rotated in order to unscrew anchor 40 from the tissue, and the entire system may be extracted from the body, or repositioned in the heart, depending on the need of a given patient.

Reference is now made to FIGS. 7A-D. FIGS. 7C-D show the decoupling and release of torque-delivering and anchor-pulling tube 208 and manipulator 206 from adapter 218 and anchor 40. This release occurs typically following the deployment of stent 50, as described hereinabove. As shown in FIG. 7A, system 200 comprises a releasable adapter holder 212 which is shaped so as to define arms 214 which have a tendency to expand radially. Holder 212 surrounds manipulator 206, as shown in FIG. 7C. During the delivery of anchor 40 toward implantation site 30 and the subsequent rotation of anchor 40 to corkscrew anchor 40 into tissue at site 30, a distal end 204 of overtube 202 is disposed adjacently to loop 216 such that a distal end portion of overtube 202 surrounds and compresses arms 214 of holder 212 (as shown in FIG. 7B). Following the pulling of anchor 40 by torque-delivering and anchor-pulling tube 208, overtube 202 is retracted slightly in order to expose arms 214 of holder 212. Responsively, arms 214 expand radially (FIG. 7C) and release adapter 218 (and thereby anchor 40) from holder 212.

As shown in FIG. 7D, overtube 202 is held in place while the physician retracts tube 208 so as to collapse and draw arms 214 into the distal end portion of overtube 202. Overtube 202 is then slid proximally within catheter 22 leaving behind anchor 40, adapter 218 coupled to anchor 40, loop 216, longitudinal member 42, and stent 50. Catheter 22, that houses overtube 202 and the components disposed therein, is extracted from the body of the patient.

Reference is again made to FIGS. 1A-D. It is to be noted that tissue-engaging elements 60a and 60b may be implanted at their respective implantation sites 30 and 50, as described hereinabove, by advancing catheter 22 and tissue-engaging elements 60a and 60b through superior vena cava 10, mutatis mutandis.

FIGS. 2A-B show a system 100 for repairing tricuspid valve 4 comprising first and second stent members 50a and 50b, first and second longitudinal members 42a and 42b, and first and second tissue anchors 40a and 40b. First tissue anchor 40a defines first tissue-engaging element 60a. First stent member 50a defines second tissue-engaging element 60b. Second tissue anchor 40b defines a third tissue-engaging element 60c. Second stent member 50b defines a fourth tissue-engaging element 60d. For some applications of the present invention, following the implantation of first tissue-engaging element 60a and second tissue-engaging element 60b, as described hereinabove with reference to FIGS. 1A-D, third and fourth tissue-engaging elements 60c and 60d are then implanted. As described hereinabove, first implantation site 30, as shown, comprises a portion of tissue that is in a vicinity of the commissure between anterior leaflet 14 and posterior leaflet 16. First implantation site 30 may comprise a portion of tissue that is between (1) the middle of the junction between the annulus and anterior leaflet 14, and (2) the middle of the junction between the annulus and posterior leaflet 16.

Following the implantation of first and second tissue-engaging elements 60a and 60b, catheter 22 is retracted from the body of the patient. Outside the body of the patient, catheter 22 is reloaded with third and fourth tissue-engaging elements 60c and 60d. Catheter 22 is then reintroduced within the body of the patient and is advanced toward right atrium 6, as shown in FIG. 2A, such that distal end 23 thereof passes through first stent member 50a and toward atrium 6. It is to be noted that a proximal end portion of longitudinal member 42a is coupled to second tissue-engaging element 60b and is not disposed within catheter 22.

Subsequently, a second tissue anchor 40b (i.e., an anchor that is similar to tissue anchor 40a, as described hereinabove) is implanted at a second portion of cardiac tissue at a third implantation site 32. Third implantation site 32 includes a portion of cardiac tissue in the vicinity of tricuspid valve 4 (e.g., a second portion of tissue of the annulus of tricuspid valve 4, as shown). Third implantation site 32, as shown, comprises a portion of tissue that is between (1) the middle of the junction between the annulus and anterior leaflet 14, and (2) the middle of the junction between the annulus and posterior leaflet 16. For some applications, third implantation site 32 may comprise a second portion of the wall that defines right atrium 6. For other applications, third implantation site 32 may comprise a portion of cardiac tissue in the right ventricle, e.g., a portion of the wall that defines the right ventricle, a ventricular portion of the annulus of valve 4, or a portion of a papillary muscle of the right ventricle.

Following implantation of third tissue-engaging element 60c, catheter 22 is retracted and tension is applied to third tissue-engaging element 60c in a manner as described hereinabove with reference to FIGS. 1C-D with regard to application of tension to implantation site 30. Additionally, tension is applied to a second longitudinal member 42b which couples third and fourth tissue-engaging elements 60c and 60d, e.g., in a manner as described hereinabove with regard to the pulling of first longitudinal member 42a, with reference to FIG. 1C. As described herein, a level of regurgitation of valve 4 is monitored during the pulling tissue of third implantation site 32 toward second implantation site 52 and of second longitudinal member 42b.

Additionally, responsively to the pulling of tissue at first and third implantation sites 30 and 32 toward second implantation site 52, anterior leaflet 14 is drawn toward septal leaflet 12, and bicuspidization is achieved. Also, responsively to the pulling, a portion of tissue that is between first and third implantation sites 30 and 32 is cinched.

Reference is now made to FIG. 2B. Once the physician determines that the regurgitation of valve 4 ceases, and valve 4 has been repaired, catheter 22 is decoupled from fourth tissue-engaging element 60d and/or from second longitudinal member 42b, and the physician retracts catheter 22 in order to expose fourth tissue-engaging element 60d, i.e., second stent member 50b, as shown. During the advancement of catheter 22 toward atrium 6, second stent member 50b is disposed within a distal portion of catheter 22 in a compressed state. Following initial retracting of catheter 22, second stent member 50b is exposed and is allowed to expand within a lumen of first stent member 50a, as shown, in order to contact a wall of inferior vena cava 8. Responsively to the expanding, second stent member 50b is implanted in second implantation site 52 and maintains the tension of second longitudinal member 42b on second tissue anchor 40b and thereby on the portion of cardiac tissue to which anchor 40b is coupled.

It is to be noted that second stent member 50b is implanted within the lumen of first stent member 50a by way of illustration and not limitation, and that for some applications of the present invention, first and second stent members 50a and 50b may be implanted coaxially at second implantation site 52.

It is to be noted that third and fourth tissue-engaging elements 60c and 60d and second longitudinal member 42b are fabricated from the same material, e.g., nitinol, from a single piece. That is, third and fourth tissue-engaging elements 60c and 60d and second longitudinal member 42b define a single continuous implant unit.

Figure 3B:
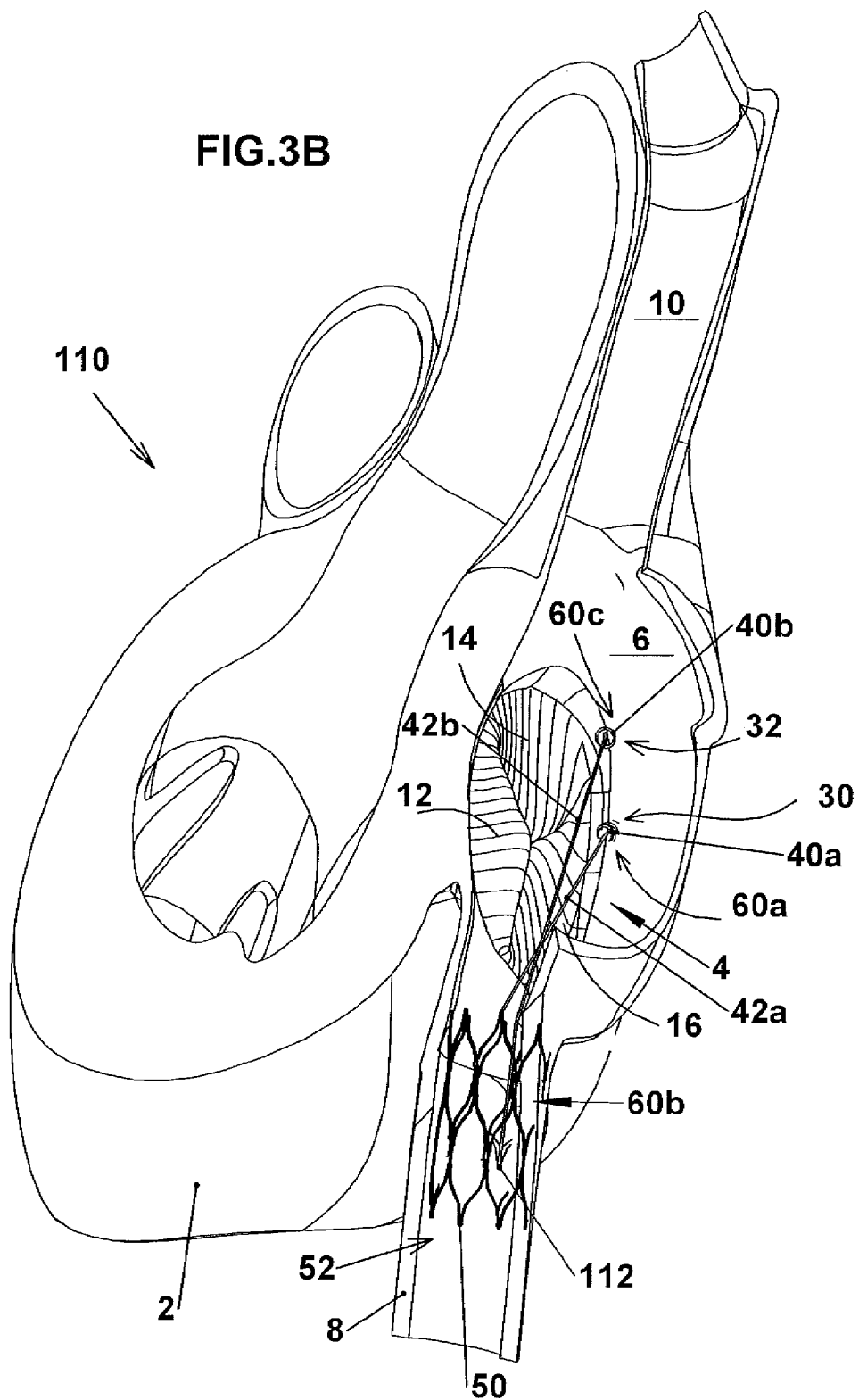

Reference is now made to FIGS. 3A-C which are schematic illustrations of a system 110 for repairing tricuspid valve 4, that comprises first, second, and third tissue-engaging elements 60a, 60b, and 60c, and first and second longitudinal members 42a and 42b, in accordance with some applications of the present invention. System 110 is similar to system 100 described hereinabove with reference to FIGS. 2A-B, with the exception that system 110 does not comprise second stent member 50b; rather, as shown in FIGS. 3B-C, a proximal end portion 112 of second longitudinal member 42b is shaped so as to define one or more engaging elements 114 (e.g., hooks or barbs, as shown). Following the implanting of third tissue-engaging element 60c and the subsequent pulling of second longitudinal member 42b, catheter 22 facilitates coupling of engaging elements 114 with the struts of stent member 50 (as shown in FIG. 3C which is an enlarged image of stent member 50 and the proximal portion of second longitudinal member 42b of FIG. 3B). The coupling of engaging elements 114 to stent 50 maintains the tension applied to longitudinal member 42, and thereby maintains the tension on third tissue-engaging element 60c in order to maintain the remodeled state of tricuspid valve 4.

It is to be noted that third tissue-engaging element 60c, second longitudinal member 42b, and engaging elements 114 and proximal end portion 112 of second longitudinal member 42b are fabricated from the same material, e.g., nitinol, from a single piece. That is, third tissue-engaging element 60c, second longitudinal member 42b, and engaging elements 114 and proximal end portion 112 of second longitudinal member 42b define a single continuous implant unit.

Reference is now made to FIGS. 2A-B and 3A-C. For some applications, following the implantation the tissue-engaging elements at their respective implantation sites, as described hereinabove, a length of each one of first and second longitudinal members 42a and 42b is adjusted by an adjustable mechanism, as described hereinbelow with reference to FIGS. 5A-B. Adjusting mechanism 150 typically comprises a mechanical element which shortens a length of each one of first and second longitudinal members 42a and 42b. For some applications, a respective adjustable mechanism 150 may be permanently coupled to each one of first and second longitudinal members 42a and 42b (not shown); each mechanism 150 comprises an adjusting element, e.g., a spool for looping respective portions of longitudinal members 42a and 42b therearound, a crimping bead for crimping and shortening respective portions of longitudinal members 42a and 42b, a ratchet element, or a deforming element which deforms respective portions of longitudinal members 42a and 42b. For other applications, adjusting mechanism 150 comprises only adjusting tool 144, as shown in FIG. 5A. In such applications, adjusting tool 144 may comprise an adjusting element, e.g., a crimping bead for crimping and shortening respective portions of longitudinal members 42a and 42b, or a deforming element which deforms respective portions of longitudinal members 42a and 42b. In either application, a level of regurgitation of valve 4 is monitored during the adjusting of the respective lengths of first and second longitudinal members 42a and 42b.

FIGS. 4A-C show a system 120 for repairing tricuspid valve 4 comprising first and second stent members 130 and 132 implanted in superior vena cava 10 and inferior vena cava, respectively, in accordance with some applications of the present invention. A catheter 122 is advanced through vasculature of the patient such that a distal end 124 of catheter 122 toward superior vena cava 10, as shown in FIG. 4A. Catheter 122 is advanced from a suitable access location, e.g., catheter 122 may be introduced into the femoral vein of the patient, through inferior vena cava 8, and toward superior vena cava 10. During the advancement of catheter 122 toward superior vena cava 10 and inferior vena cava 8, stent members 130 and 132 are disposed within a distal portion of catheter 122 in a compressed state.

In FIG. 4B, first stent 130 is deployed from within catheter 122 and expands to contact tissue of a wall of superior vena cava 10. This portion of the wall of the superior vena cava defines first implantation site 30 in such applications of the present invention. Additionally, first stent member 130 defines first tissue-engaging element 60a in such applications of the present invention. It is to be noted that the portion of superior vena cava 10 in which stent 130 is implanted defines a portion of tissue that is in the vicinity of valve 4.

Catheter 122 is then retracted so as to pull and apply tension to longitudinal member 42. Longitudinal member 42 is pulled directly by catheter 122 and/or indirectly by pulling stent member 132 disposed within catheter 122. During the pulling, a level of regurgitation of tricuspid valve 4 is monitored, because responsively to the pulling, the geometry of the wall of atrium 6 is altered and the leaflets of tricuspid valve 4 are drawn together so as to reduce and eliminate regurgitation of valve 4.

Once the physician determines that the regurgitation of valve 4 ceases, and valve 4 has been repaired, the physician decouples catheter 122 from second stent member 132 disposed therein and/or from longitudinal member 42, and then retracts catheter 122 in order to expose second tissue-engaging element 60b, i.e., second stent member 132, as shown. Following initial retracting of catheter 122, second stent member 132 is exposed and is allowed to expand and contact a wall of inferior vena cava 8, as shown in FIG. 4C. Responsively to the expanding, second stent member 132 is implanted in second implantation site 52 and maintains the tension of longitudinal member 42 on first stent member 130 and thereby maintains the altered geometry of the wall of atrium 6 and of the leaflets of tricuspid valve 4.

Reference is again made to FIGS. 4A-C. For some applications, following the deploying of first and second tissue-engaging elements 60a and 60b (i.e., first and second stent members 130 and 132, respectively), a distance between first and second tissue-engaging elements 60a and 60b is adjusted by an adjustable mechanism, as described hereinbelow with reference to FIGS. 5A-B. In such applications, a length of longitudinal member 42 between first and second stent members 130 and 132 may be adjusted by an adjusting mechanism 150, as shown in FIGS. 5A-B. Adjusting mechanism 150 typically comprises a mechanical element which shortens a distance of longitudinal member 42 between first and second stent members 130 and 132. For some applications, adjustable mechanism 150 may be permanently coupled to longitudinal member 42 (not shown) and comprises an adjusting element, e.g., a spool for looping portions of longitudinal member 42 therearound, a crimping bead for crimping and shortening a portion of longitudinal member 42, a ratchet element, or a deforming element which deforms a portion of longitudinal member 42 in order to shorten its length between first and second stent members 130 and 132. For other applications, adjusting mechanism 150 comprises only adjusting tool 144, as shown in FIG. 5A. In such applications, adjusting tool 144 may comprise an adjusting element, e.g., a crimping bead for crimping and shortening a portion of longitudinal member 42, or a deforming element which deforms a portion of longitudinal member 42 in order to shorten its length between first and second stent members 130 and 132. In either application, a level of regurgitation of valve 4 is monitored during the adjusting of the distance between first and second tissue-engaging elements 60a and 60b by adjusting mechanism 150.

It is to be noted that first and second stent members 130 and 132 and longitudinal member 42 are fabricated from the same material, e.g., nitinol, from a single piece. That is, first and second stent members 130 and 132 and longitudinal member 42 define a single continuous implant unit.

Reference is yet again made to FIGS. 4A-C. It is to be noted that distal end 124 of catheter 122 may first be advanced toward inferior vena cava, and not first toward superior vena cava, as shown in FIG. 4A. In such an embodiment, catheter 122 may be introduced into the external jugular vein, through the subclavian vein, through superior vena cava 10, and toward inferior vena cava 8. Alternatively, catheter 122 may be introduced into the basilic vein, through the subclavian vein, through superior vena cava 10 and toward inferior vena cava 8. It is to be noted that any suitable access location may be used to introduce catheter 122 into the vasculature of the patient.

Reference is now made to FIGS. 5A-B which are schematic illustrations of a system 140 for repairing tricuspid valve 4 comprising first and second tissue anchors 40a and 40b coupled together by longitudinal member 42, in accordance with some applications of the present invention. In such applications, first tissue anchor 40a defines first tissue-engaging element 60a, and second tissue anchor 40b defines second tissue-engaging element 60b. Tissue anchors 40a and 40b may comprise any suitable anchor for puncturing, squeezing, or otherwise engaging cardiac tissue of the patient. As shown by way of illustration and not limitation, tissue anchors 40a and 40b comprise helical tissue anchors which puncture and corkscrew into the cardiac tissue. It is to be noted that first and second tissue-engaging elements 60a and 60b (i.e., first and second tissue anchors 40a and 40b) and longitudinal member 42 are fabricated from the same material, e.g., nitinol, from a single piece. That is, first and second tissue-engaging elements 60a and 60b and longitudinal member 42 define a single continuous implant unit.

Catheter 142 is advanced through vasculature of the patient, in manner as described hereinabove with regard to catheter 22 with reference to FIG. 1A. Catheter 142 is advanced toward first implantation site 30 and facilitates implantation of first tissue anchor 40a in the cardiac tissue. As shown, first implantation site 30 includes a first portion of tissue of the annulus of valve 4 at the mural side of valve 4, by way of illustration and not limitation. For some applications, first implantation site 30 may include a first portion of the wall of atrium 6 of heart 2. As shown by way of illustration and not limitation, first implantation site includes a portion of tissue of the annulus at the commissure between anterior leaflet 14 and posterior leaflet 16. It is to be noted that first implantation site 30 may be implanted at any suitable location along and in the vicinity of the annulus of valve 4.

Catheter 142 is then advanced toward second implantation site 52 and facilitates implantation of second tissue anchor 40b in the cardiac tissue. For some applications, as catheter 142 is advanced toward second implantation site, longitudinal member 42 is pulled to draw together the leaflets of valve 4, while a level of regurgitation of valve 4 is monitored. As shown, second implantation site 52 includes a second portion of tissue of the annulus of valve 4 at the septal side of valve 4, by way of illustration and not limitation. For some applications, second implantation site 52 may include a second portion of the wall of atrium 6 of heart 2. As shown by way of illustration and not limitation, second implantation site 52 includes a portion of tissue of the annulus inferior of the middle of septal leaflet 12. It is to be noted that first implantation site 30 may be implanted at any suitable location along and in the vicinity of the annulus of valve 4, e.g., at the commissure between posterior leaflet 16 and septal leaflet 12.

For such an application, by applying tension to longitudinal member 42, anterior leaflet 14 and septal leaflet 12 are drawn together, and bicuspidization of valve 4 is achieved. For some applications, during the adjusting of mechanism 150, a retrievable stent may be deployed in inferior vena cava 8 so as to stabilize system 140 during the adjusting of adjusting mechanism 150. It is to be further noted that tissue-engaging elements 60a and 60b and catheter 142 may be advanced toward atrium 6 through superior vena cava, mutatis mutandis.

For some applications of the present invention, system 140 comprises one or more anchor-manipulating tools (not shown for clarity of illustration), that is slidably disposed within catheter 142. The anchor-manipulating tool is slid distally with within catheter 142 so as to push distally tissue anchors 40a and 40b and expose tissue anchors 40a and 40b from within catheter 142. For some applications of the present invention, the anchor-manipulating tool(s) is(/are) reversibly couplable to anchors 40a and 40b, and facilitate(s) implantation of anchors 40a and 40b in the cardiac tissue. For applications in which anchors 40a and 40b comprises respective helical tissue anchor, as shown, the operating physician rotates the anchor-manipulating tool(s) from a site outside the body of the patient in order to rotate anchors 40a and 40b, and thereby corkscrew at least respective distal portions of anchors 40a and 40b in the cardiac tissue.

Reference is again made to FIGS. 5A-B. It is to be noted that first and second implantation sites 30 and 52 include cardiac tissue that is upstream of valve 4 by way of illustration and not limitation, and that either or both first and second implantation sites may include cardiac tissue that is downstream of valve 4.

Typically, following implantation of first and second tissue anchors 40a and 40b, a length of longitudinal member 42, that is disposed between first and second tissue anchors 40a and 40b, is adjusted by adjusting mechanism 150. Adjusting mechanism 150 typically comprises a mechanical element which shortens a distance of longitudinal member 42 between first and second tissue-engaging elements 60a and 60b. For some applications, adjustable mechanism 150 may be permanently coupled to longitudinal member 42 (as shown in FIG. 5B) and comprises an adjusting element, e.g., a spool for looping portions of longitudinal member 42 therearound, a crimping bead for crimping and shortening a portion of longitudinal member 42, a ratchet element, or a deforming element which deforms a portion of longitudinal member 42 in order to shorten its length between first and second tissue-engaging elements 60a and 60b.

For other applications, adjusting mechanism 150 comprises only adjusting tool 144, as shown in FIG. 5A. In such applications, adjusting tool 144 may comprise an adjusting element, e.g., a crimping bead for crimping and shortening a portion of longitudinal member 42, or a deforming element which deforms a portion of longitudinal member 42 in order to shorten its length between first and second tissue-engaging elements 60a and 60b.

In either application, a level of regurgitation of valve 4 is monitored during the adjusting of the distance between first and second tissue-engaging elements 60a and 60b by adjusting mechanism 150.

Following the adjusting of the distance between first and second implantation sites 30 and 52, adjusting tool 144 and catheter 142 are decoupled from longitudinal member 42 and are extracted from the body of the patient.

Reference is now made to FIG. 6 which is a schematic illustration of a system 700 for repairing tricuspid valve 4 comprising first tissue-engaging element 60a implanted at a portion of the annuls of valve 4 and a third tissue-engaging element 60c implanted at a portion of a papillary muscle 72 in the right ventricle of the patient, in accordance with some applications of the present invention. It is to be noted that third implantation site 32 comprises papillary muscle 72 by way of illustration and not limitation, and that third implantation site 32 may comprise any potion of a wall of the right ventricle (e.g., a portion of tissue of the annulus at the ventricular surface of valve 4, a portion of the wall of the ventricle in the vicinity of valve 4, a portion of tissue in the vicinity of the apex of heart 2, or any other suitable portion of the wall of the ventricle).

Reference is now made to FIGS. 2A-B and 6. First, second, and third tissue-engaging elements 60a-c of FIG. 6 are implanted in cardiac tissue in a manner as described hereinabove with reference to FIGS. 2A-B, with the exception that, in order to implant third tissue-engaging element 60c, catheter 22 passes through the leaflets of valve 4 into the right ventricle and implants third tissue-engaging element 60c in tissue of the ventricle. Following coupled of third tissue-engaging element 60c in FIG. 6, second stent 50b is deployed in second implantation site 52 in inferior vena cava 8, as described hereinabove with reference to FIG. 2B.

Reference is now made to FIGS. 3A-C and 6. It is to be noted, that for some applications, second longitudinal member 42b is coupled at a proximal end thereof to one or more barbs 114 (i.e., and is not connected to second stent 50, as shown). Barbs 114 enable second longitudinal member 42b to be coupled to stent 50 that is in connection with first longitudinal member 42a, and thereby maintain tension on third implantation site 32 and maintain coaptation of at least anterior leaflet 14 and septal leaflet 12.

Reference is again made to FIG. 6. Such an application of at least one tissue-engaging element 60 in a portion of tissue of the ventricle of heart 2, in some applications, facilitates independent adjustment of valve 4 and a portion of the ventricle wall of heart 2. That is, for some application, geometric adjustment of the right ventricle to improve its function is achieved.

For some applications, following the deploying of first, second, third, and fourth tissue-engaging elements 60a-d (i.e., first and second anchors 40a and 40b, and first and second stents 50a and 50b), (1) a distance between first and second tissue-engaging elements 60a and 60b is adjustable by first adjustable mechanism, and (2) a distance between third and fourth tissue-engaging elements 60c and 60d is adjustable by a second adjustable mechanism, as described hereinbelow with reference to FIGS. 5A-B. In such applications, (1) a length of first longitudinal member 42a between first and second tissue-engaging elements 60a and 60b may be adjusted by a first adjusting mechanism 150, as shown in FIGS. 5A-B, and (2) a length of second longitudinal member 42b between third and fourth tissue-engaging elements 60c and 60d may be adjusted by a second adjusting mechanism 150, as shown in FIGS. 5A-B. Adjusting mechanisms 150 typically each comprise a mechanical element which shortens a distance of respective longitudinal members 42a and 42b. For some applications, adjustable mechanisms 150 may be permanently coupled to respective longitudinal members 42a and 42b (not shown) and each comprise an adjusting element, e.g., a spool for looping portions of longitudinal members 42a and 42b therearound, a crimping bead for crimping and shortening respective portions of longitudinal members 42a and 42b, a ratchet element, or a deforming element which deforms respective portions of longitudinal members 42a and 42b in order to shorten its length between the respective tissue-engaging elements 60. For other applications, adjusting mechanisms 150 each comprise only adjusting tool 144, as shown in FIG. 5A. In such applications, adjusting tool 144 may comprise an adjusting element, e.g., a crimping bead for crimping and shortening respective portions of longitudinal members 42a and 42b, or a deforming element which deforms respective portions of longitudinal members 42a and 42b. In either application, a level of regurgitation of valve 4 is monitored and the adjustment of the geometry of the right ventricle is monitored during (1) the adjusting of the distance between first and second implantation sites 30 and 52, and (2) the adjusting of the distance between third and second implantation sites 32 and 52, respectively.

Reference is now made to FIGS. 1A-D, 2A-B, 3A-C, 4A-C, 5A-B, 6, and 7A-D. It is to be noted that apparatus and methods described herein for repairing tricuspid valve 4 may also be applied to repair any other heart valve of the patient, e.g., a mitral valve, a pulmonary valve, or an aortic valve. For such applications, second implantation site 52 may include a portion of a blood vessel that is in contact with the left atrium of the patient, e.g., a pulmonary vein, a portion of the wall of the left atrium, a portion of the annulus of the mitral valve, or a portion of the left ventricle of the heart of the patient, and first implantation site 30 may include a portion of the wall of the left atrium, a portion of the annulus of the mitral valve, or a portion of the left ventricle of the heart of the patient.

Reference is again made to FIGS. 1A-D, 2A-B, 3A-C, 4A-C, 5A-B, 6, and 7A-D. It is to be noted that any suitable number of tissue-engaging elements 60 may be implanted in and/or grasp cardiac tissue, depending on the needs of a given patient. Typically, one or more tissue-engaging elements 60 is/are implanted in cardiac tissue (e.g., tissue of the annulus, tissue of the wall of the atrium adjacent the valve, or tissue of the wall of the ventricle adjacent the valve) in a vicinity of the valve that is between the middle of the anterior leaflet and the middle of the posterior leaflet, e.g., at the commissure between the middle of the anterior leaflet and the middle of the posterior leaflet. For such an application, pulling together implantation sites 30 and 52 pulls anterior leaflet 14 toward septal leaflet 12 and thereby achieves bicuspidization of tricuspid valve 4. It is to be noted, however, that tissue engaging elements 60 may be implanted in portions of tissue in the vicinity of any portion of the annulus of valve 4.

Reference is yet again made to FIGS. 1A-D, 2A-B, 3A-C, 4A-C, and 5A-B, 6, and 7A-D. It is to be noted that the adjustment of the distance between the respective implantation sites of the tissue-engaging elements 60 is facilitated by adjusting mechanism 150 following initial implantation of the tissue-engaging elements 60 and the repair of the valve and/or the adjustment of the heart wall geometry.

For some applications, techniques described herein are practiced in combination with techniques described in one or more of the references cited in the Background section of the present patent application.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method, comprising:
 implanting at least a first tissue-engaging element in a first portion of tissue in a vicinity of a tricuspid valve of a patient;
 implanting at least a second tissue-engaging element in a portion of a blood vessel selected from the group of blood vessels consisting of: a superior vena cava and an inferior vena cava; and
 drawing at least a first leaflet of the tricuspid valve toward at least a second leaflet of the tricuspid valve by performing a tensioning method selected from the group consisting of:
 (a) adjusting a distance between the portion of the blood vessel and the first tissue portion, and maintaining the adjusted distance using tension applied to the first tissue-engaging element and the second tissue-engaging element by a longitudinal member that connects the first and the second tissue-engaging elements, and
 (b) adjusting the distance between the portion of the blood vessel and the first tissue portion by applying tension to the first tissue-engaging element and the second tissue-engaging element using the longitudinal member.

2. The method according to claim 1, wherein adjusting the distance between the portion of the blood vessel and the first tissue portion comprises pulling the longitudinal member that connects the first and second tissue-engaging elements.

3. The method according to claim 1, further comprising monitoring repair of the tricuspid valve in conjunction with the adjusting the distance between the portion of the blood vessel and the first tissue portion.

4. The method according to claim 1, wherein adjusting the distance between the portion of the blood vessel and the first tissue portion of tissue comprises pulling the first tissue-engaging element toward the portion of the blood vessel.

5. The method according to claim 1, wherein adjusting the distance between the portion of the blood vessel and the first tissue portion comprises achieving bicuspidization of the tricuspid valve.

6. The method according to claim 1, wherein adjusting the distance between the portion of the blood vessel and the first tissue portion comprises actuating an adjusting mechanism that is coupled to a portion of the longitudinal member that connects the first and second tissue-engaging elements.

7. The method according to claim 1, wherein the second tissue-engaging element comprises a stent, and wherein implanting the second tissue-engaging element in the portion of the blood vessel comprises expanding the stent in the portion of the blood vessel.

8. The method according to claim 1, wherein implanting the first tissue-engaging element in the first tissue portion comprises engaging the first portion of tissue by performing one or more actions selected from the group consisting of: puncturing and squeezing the first tissue portion and advancing at least a portion of the first tissue-engaging element into the first tissue portion.

9. The method according to claim 8, wherein:
the first tissue portion includes a portion of tissue of that is opposite the portion of the blood vessel of the patient,
engaging the first tissue portion comprises engaging the portion of tissue that is opposite the portion of the blood vessel of the patient, and
drawing the first leaflet of the tricuspid valve toward the second leaflet of the tricuspid valve comprises adjusting a distance between the portion of the blood vessel of the patient and the portion of tissue that is opposite the portion of the blood vessel of the patient.

10. The method according to claim 8, wherein the first tissue portion includes a portion of tissue of a wall of a right atrium of the heart above an annulus of the tricuspid valve, and wherein engaging the first tissue portion comprises engaging the portion of tissue of the wall of the right atrium.

11. The method according to claim 8, wherein the first tissue portion includes a portion of tissue of an annulus of the valve, and wherein engaging the first tissue portion comprises engaging the portion of tissue of the annulus of the valve.

12. The method according to claim 11, wherein the portion of tissue of the annulus of the valve includes a portion of tissue that is between a middle portion of an anterior leaflet of the valve and a middle portion of a posterior leaflet of the valve.

13. The method according to claim 1, wherein performing the tensioning method comprises adjusting the distance between the portion of the blood vessel and the first tissue portion, and maintaining the adjusted distance using the tension applied to the first tissue-engaging element and the second tissue-engaging element by the longitudinal member.

14. The method according to claim 1, wherein performing the tensioning method comprises adjusting the distance between the portion of the blood vessel and the first tissue portion by applying tension to the first tissue-engaging element and the second tissue-engaging element using the longitudinal member.

15. The method according to claim 1, wherein implanting the first tissue-engagement element comprises advancing a catheter through vasculature of the patient to the vicinity of the tricuspid valve, and deploying the first tissue-engaging element from the catheter.

16. The method according to claim 2, wherein pulling the longitudinal member comprises pulling the longitudinal member prior to implanting the second tissue-engaging element.

17. The method according to claim 2, wherein adjusting the distance between the portion of the blood vessel and the first portion of tissue in the vicinity of the tricuspid valve comprises pulling on the second tissue-engaging element in order to pull the longitudinal member.

18. The method according to claim 3, wherein monitoring the repair of the tricuspid valve comprises monitoring the drawing together of the first and the second leaflets of the tricuspid valve.

19. The method according to claim 3, wherein monitoring the repair of the tricuspid valve comprises monitoring a level of regurgitation of the tricuspid valve in conjunction with the adjusting the distance.

20. The method according to claim 7, wherein expanding the stent comprises expanding the stent in the portion of the blood vessel so as to allow free flow of blood through the stent throughout a cardiac cycle of the patient.

* * * * *